United States Patent
Kwon et al.

(10) Patent No.: US 11,396,555 B2
(45) Date of Patent: *Jul. 26, 2022

(54) MONOCLONAL ANTIBODY WHICH SPECIFICALLY RECOGNIZES B CELL LYMPHOMA AND USE THEREOF

(71) Applicant: Eutilex Co., Ltd., Seoul (KR)

(72) Inventors: Byoung Se Kwon, Seoul (KR); Kwang-Hui Kim, Seoul (KR); Young-Ho Kim, Seoul (KR); Ho-sik Oh, Seoul (KR); Don-Gil Lee, Seoul (KR); Seung-Joo Lee, Seoul (KR); Beom-Kyu Choi, Seoul (KR); Insoo Park, Seoul (KR); Chungyong Han, Seoul (KR)

(73) Assignee: Eutilex Co., Ltd., Seoul (KR)

( * ) Notice: Subject to any disclaimer, the term of this patent is extended or adjusted under 35 U.S.C. 154(b) by 432 days.

This patent is subject to a terminal disclaimer.

(21) Appl. No.: 16/358,636

(22) Filed: Mar. 19, 2019

(65) Prior Publication Data

US 2019/0375851 A1 Dec. 12, 2019

Related U.S. Application Data

(60) Continuation of application No. 15/829,048, filed on Dec. 1, 2017, now Pat. No. 10,233,254, which is a division of application No. 14/639,679, filed on Mar. 5, 2015, now Pat. No. 9,862,775.

(30) Foreign Application Priority Data

Mar. 5, 2014 (KR) ........................ 10-2014-0026252

(51) Int. Cl.
*C07K 16/30* (2006.01)
*C07K 16/28* (2006.01)
*G01N 33/574* (2006.01)
*G01N 33/577* (2006.01)
*A61K 47/68* (2017.01)
*A61K 39/00* (2006.01)

(52) U.S. Cl.
CPC ...... *C07K 16/3061* (2013.01); *A61K 47/6829* (2017.08); *A61K 47/6867* (2017.08); *C07K 16/28* (2013.01); *C07K 16/2833* (2013.01); *G01N 33/577* (2013.01); *G01N 33/57426* (2013.01); *A61K 2039/505* (2013.01); *C07K 2317/24* (2013.01); *C07K 2317/622* (2013.01); *C07K 2317/732* (2013.01); *C07K 2319/03* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 5,459,127 | A | 10/1995 | Felgner |
| 5,580,859 | A | 12/1996 | Felgner |
| 5,589,466 | A | 12/1996 | Felgner |
| 5,693,622 | A | 12/1997 | Wolff |
| 9,862,775 | B2 | 1/2018 | Kwon et al. |
| 10,233,254 | B2 | 3/2019 | Kwon |
| 2016/0257762 | A1 | 9/2016 | Kwon et al. |
| 2020/0165342 | A1 | 5/2020 | Kwon |
| 2020/0237821 | A1 | 7/2020 | Kwon |

FOREIGN PATENT DOCUMENTS

| | | |
|---|---|---|
| CA | 2012311 | 9/1990 |
| KR | 100701923 | 3/2007 |
| WO | WO 1988/07085 | 9/1988 |
| WO | WO 1988/07086 | 9/1988 |
| WO | WO 1988/09344 | 12/1988 |
| WO | WO 1995/21931 | 8/1995 |
| WO | WO 1996/17823 | 6/1996 |
| WO | WO 1995/18863 | 7/1996 |
| WO | WO 1996/25508 | 8/1996 |
| WO | WO 2012/007900 | 1/2012 |
| WO | WO2015/133817 | 9/2015 |
| WO | WO 2016/090190 | 6/2016 |
| WO | WO 2016/094304 | 6/2016 |

(Continued)

OTHER PUBLICATIONS

Moore et al (VP, 49(4):658-669, 2012).*
Arescu et al (VS, 8, 120, Jan. 11, 2021).*
EP Extended Search Report in European Appln No. 18757730.9, dated Oct. 9, 2020, 7 pages.
Turtle et al., "Durable molecular remissions in chronic lymphocytic leukemia treated with CD19-specific chimeric antigen receptor-modified T cells after failure of ibrutinib," Journal of Clinical Oncology, Sep. 10, 2017, 35:26.
Ahn, "New monoclonal antibody that can inhibit the growth of L3055 Burkitt's lymphoma cells and HK follicular dendritic cells," Master's Thesis of Science, Graduate School of University of Ulsan, 35 pages, English abstract, 2008.

(Continued)

*Primary Examiner* — Brad Duffy
(74) *Attorney, Agent, or Firm* — Oblon, McClelland, Maier & Neustadt, L.L.P.

(57) ABSTRACT

Provided is a monoclonal antibody which specifically recognizes B cell lymphoma cells and a use thereof. More specifically, provided are the monoclonal antibody; a pharmaceutical composition for preventing or treating B cell lymphoma including the monoclonal antibody; a composition for diagnosing B cell lymphoma including the monoclonal antibody; a method for providing information for diagnosing B cell lymphoma using the monoclonal antibody; a chimeric antigen receptor (CAR) protein including i) the antibody, ii) a transmembrane domain, and iii) an intracellular signaling domain; a recombinant vector which expresses the CAR protein; a CAR-modified T cell transformed with the recombinant vector; a pharmaceutical composition for preventing or treating B cell lymphoma including the CAR-modified T cell; and an antibody-drug conjugate wherein the monoclonal antibody and a drug are conjugated.

11 Claims, 10 Drawing Sheets

Specification includes a Sequence Listing.

(56) References Cited

FOREIGN PATENT DOCUMENTS

| WO | WO 2016/197064 | 12/2016 |
|----|----------------|---------|
| WO | WO 2017/011804 | 1/2017 |
| WO | WO 2017/096329 | 6/2017 |
| WO | WO 2018/005559 | 1/2018 |
| WO | WO 2018/057904 | 3/2018 |

OTHER PUBLICATIONS

Gusso et al., "Humanization of Monoclonal Antibodies," Methods in Enzymology, 203: 99-121, 1991.
Han et al., "Selective killing of malignant B cells using T cells redirected against malignancy variant receptor," Journal for Immunotherapy of Cancer, 2(Suppl 3): 16, 2014.
Henne et al., "Surface expression of the invariant chain (CD74) is independent of concomitant expression of major histocompatibility complex class II antigens,", Immunology, 84: 177-182, 1995.
International Search Report and Written Opinion in International Appln. No. PCT/KR2015/002089, dated Jul. 6, 2015.
Liu et al., "Up-regulation of vascular endothelial growth factor-D expression in clear cell renal cell carcinoma by CD74: a critical role in cancer cell tumorigenesis," J. Immunol., 181: 6584-6594, 2008.
Mariuzza et al., "The structural basis of antigen-antibody recognition," Annu. Rev. Biophys. Biophys. Chem., 16: 139-159, 1987.
Porter et al., "Chimeric antigen receptor-modified T cells in chronic lymphoid leukemia," N. Engl. J. Med., 365:725-733, 2011.
Savoldo et al., "CD28 costimulation improves expansion and persistence of chimeric antigen receptor-modified T cells in lymphoma patients," J. Clin. Invest., 121(5): 1822-1826, 2011.
Van Meerten et al., "Novel antibodies against follicular non-Hodgkin's lymphoma," Best Pract. Res. Clin. Haematol., 24(2): 231-526, 2011.
Winkler et al., "Changing the antigen binding specificity by single point mutations of an anti-p24 (HIV-1) antibody," J. Imm., 265: 4505-4514, 2000.
Anderton & Wraith, "Selection and fine-tuning of the autoimmune T-cell repertoire," Nat. Rev. Immunol., 2: 487-498, 2002.
Baniyash, "TCR zeta-chain downregulation: curtailing an excessive inflammatory immunce response," Nat. Rev. Immunol., 4: 675-687, 2004.
Beal et al., "Kinetics of early T cell receptor signaling regulate the pathway of lytic granule delivery to the secretory domain," Immunity, 632-642, 2009.
Blackburn et al., "Coregulation of CD8+ T cell exhaustion by multiple inhibitory receptors during chronic viral infection," Nat. Immunol., 10: 29-37, 2009.
Brown et al., "Regression of glioblastoma after chimeric antigen receptor T-cell therapy," N. Engl. J. Med., 375: 2561-2569, 2016.
Caruso et al., "Tuning sensitivity of CAR to EGFR density limits recognition of normal tissue hwile maintaining potent antitumor activity," Cancer Res., 75: 3505-3518, 2015.
Chang et al., "Identification and selective expansion of funtionally superior T cells expressing chimeric antigen receptors," J. Transl. Med., 13: 161, 2015.
Chen and Okayama, "High-Efficiency Transformation of Mammalian Cells by Plasmid DNA", Mol. Cell. Biol. 7: 2745-2752, 1987.
Chiu et al., "Sprouty-2 regulates HIV-specific T cell polyfunctionality," J. Clin. Invest., 124(1): 198-208, 2014.
Curiel et al., "High-Efficiency Gene Transfer Mediated by Adenovirus Coupled to DNA-Polylysine Complexes", Hum. Gene Ther. 3: 147-154, 1992.
Danjoh et al., "Development of a robust method for establishing B cell lines using Epstein-Barr virus," In Veitro Cell. Dev. Biol Anim., 48: 393-402, 2012.
Davila et al., "Efficacy and toxicity management of 19-28z CAR T cell therapy in B cell acute lymphoblastic leukemia," Sci. Transl. Med., 2014, 6: 224ra225, 2014.
Denardo et al., "Direct antilymphoma effects on human lymphoma cells of monotherapy and combination therapy with CD20 and HLA-DR antibodies and 90Y-labeled HLA-DR antibodies," Clin. Cancer Res., 11(19 Suppl): 7075s-7079s, 2005.
Ding et al., "Polyfunctional CD4(+) T cells are essnetial for eradicating advanced B-cell lymphoma after chemotherapy," Blood, 120: 2229-2239, 2012.
Eyquem et al., "Targeting a CAR to the TRAC locus with CRISPR/Cas9 enhances tumour rejection," Nature, 543: 113-117, 2017.
Fedorov et al., "PD-1- and CTLA-4-based inhibitory chimeric antigen receptors (iCARs) divert off-target immunotherapy responses," Sci. Transl. Med., 5: 215ra172, 2013.
Feigner et al., "Lipofection: a highly efficient, lipid-mediated DNA-transfection procedure.", Proc. Natl. Acad. Sci. USA. 84: 7413-7417, 1987.
Franzese et al., "Polyfunctional Melan—A-specific tumor-reactive CD8(+) T cells elicited by dacarbazine treatment before peptide-vaccination depends on AKT activation sustsained by ICOS," Oncoimmunology, 5: e1114203, 2016.
Frigault et al., "Identification of chimeric antigen receptors that mediate constitutive or inducible proliferation of T cells," Cancer Immunol. Res., 3: 356-367, 2015.
Gallegos et al., "Control of T cell antigen reactivity via programmed TCR downregulation," Nat. Immunol., 17: 379-386, 2016.
Gatzka et al., "Altered thymic selection and increased autoimmunity caused by ectopic expression of DRAK2 during T cell development," J. Immunol., 183: 285-297, 2009.
Gomes-Silva et al., "CD7-edited T cells expressing a CD7-specific CAR for the therapy of T-cell malignancies," Blood, 130: 285-296, 2017.
Gopal, "Gene Transfer Method for Transient Gene Expression, Stable Transformation, and Cotransformation of Suspension Cell Cultures", Mol. Cell Biol., 5: 1188-1190, 1985.
Grupp et al., "Chimeric antigen receptor-modified T cells for acute lymphoid leukemia," N. Engl. J. Med., 368: 1509-1518, 2013.
Han et al., "Adnectin-based design of chimeric antigen receptor for T cell engineering," Mol., Ther., 25: 2466-2476, 2017.
Han et al., "Desensitized chimeric antigen receptor cells selectively recognize target cells with enhanced antigen expression," Nature Communications, 9: article 468, 2018.
Huijbers et al., "Minimal tolerance to a tumor antigen encoded by a cancer-germline gene," J. Immunol., 188: 111-121, 2012.
Ichim & Wells, "Generation of high-titer viral preparations by concentration using successive rounds of ultracentrifugation," J. Transl. Med., 9: 137, 2011.
International Search Report and Written Opinion in International Appln. No. PCT/IB2018/000227, dated Jun. 28, 2018, 5 pages.
Ivanov et al., "Monoclonal antibodies directed to CD20 and HLA-DR can elicit homotypic adhesion followed by lysosome-mediated cell death in human lymphoma and leukemia cells," J. Clin. Invest., 119: 2143-2159, 2009.
Jedema et al., "New CFSE-based assay to determine susceptibility to lysis by cytotoxic T cells of leukemic precursor cells within a heterogeneous target cell population," Blood, 103: 2677-2682, 2004.
Jenkins et al., "The strength of T cell receptor signal controls the polarization of cytotoxic machinery to the immunological synapse," Immunity, 31: 621-631, 2009.
Johnson & June, "Driving gene-engineered T cell immunotherapy of cancer," Cell Research, 27: 38-58, 2017.
Kalos et al., "T cells with chimeric antigen receptors have potent antitumor effects and can establish memory in pateints with advanced leukemia," Sci. Transl. Med., 3: 95ra73, 2011.
Kochenderfer et al., "B-cell depletion and remissions of malignancy along with cytokine-associated toxicity in a clinical trial of anti-CD 19 chimeric-antigen-receptor-transduced T cells," Blood, 119: 2709-2720, 2012.
Kochenderfer et al., "Chemotherapy-refractory diffuse large B-cell lymphoma and indolent B-cell malignancies can be effectively treated with autologous T cells expressing an anti-CD19 chimeric antigen receptor," J. Clin. Oncol., 33: 540-549, 2015.
Kochenderfer et al., "Eradication of B-lineage cells and regression of lymjphoma in a patient treated with autologous T cells genetically engineered to recognize CD19," Blood, 116: 4099-4102, 2010.

(56) References Cited

OTHER PUBLICATIONS

Kumar et al., "Increased sensitivity of antigen-experienced T cells through the enrichment of oligomeric T cell receptor complexes," Immunity, 35: 375-387, 2011.

Lamers et al., "Treatment of metastatic renal cell carcinoma with autologous T-lymphocytes genetically retargeted against carbonic anhydrase IX: first clinical experience," J. Clin. Oncol., 24: e20-22, 2006.

Lieberman, "The ABCs of granule-mediated cytotoxicity: new weapons in the arsenal," Nat. Rev. Immunol., 3:361-370, 2003.

Lin et al., "A phase I/II dose escalation study of apolizumab (Hu1D10) using a stepped-up dosing schedule in pateitns with chronic lymphocytic leukemia and acute leukemia," Leuk. Lymphoma, 50: 1958-1963, 2009.

Liu et al., "Affinity-tuned ErbB2 or EGFR chimeric antigen receptor T cels exhibit an increased therapeutic index against tumors in mice," Cancer Res., 75: 3596-3607, 2015.

Long et al., "4-1BB costimulation ameliorates T cell exhaustion induced by tonic signaling of chimeric antigen receptors," Nat. Med., 21: 581-590, 2015.

Machey et al., "Gene transfer from targeted liposomes to specific lymphoid cells by electroporation", Proc. Natl. Acad. Sci. USA 85: 8027-8031, 1988.

Mamonkin et al., "T-cell-directed chimeric antigen receptor for the selective treatment of T-cell malignancies," Blood, 126: 983-992, 2015.

Mandl et al., "T cell-positive selection uses self-ligand binding strength to optimize repertoire recognition of foreign antigens," Immunity, 38: 263-274, 2013.

Martinez-Lostao et al., "How do cytotoxic lymphocytes kill cancer cells?" Clin. Cancer. Res., 21: 5047-5056, 2015.

Maus et al., "Antibody-modified T cells: CARs take the front seat for hematologic malignancies," Blood, 123: 2625-2635, 2014.

Milone et al., "Chimeric receptors containing CD137 signal transduction domains mediate enhanced survival of T cells and increased antileukemic efficacy in vivo," Mol. Ther., 17: 1453-1464, 2009.

Morgan et al., "Case report of a serious adverse event following the administration of T cells transduced with a chimeric antigen receptor recognizing ERBB2," Mol. Ther., 18: 843-851, 2010.

Nagy et al., "Fully human, HLA-DR-specific monoclonal antibodies efficiently induce programmed death of malignant lymphoid cells," Nat. Med., 8: 801-807, 2002.

Pageon et al., "Functional role of T-cell receptor nanoclusters in signal initiation and antigen discrimination," Proc. Natl. Acad. Sci. USA, 113: E5454-5463, 2016.

Rufener, et al., "Preserved activity of CD20-specific chimeric antigen receptor-expressing T cells in the presnece of Rituximab," Cancer Immunol. Res., 2016, 4:509-519.

Sebzda et al., "Selection of the T cell repoertoire," Annu. Rev. Immunol., 17: 829-874, 1999.

Shackelford et al., "HLA-DR antigens: structure, separation of subpopulations, gene cloning and function," Immunol. Rev., 66: 133-187, 1982.

Speiser et al., "Regulatory circuits of T cell function in cancer," Nat. Rev. Immunol., 16: 599-611, 2016.

Taylor et al., "A DNA-based T cell receptor reveals a role for receptor clustering in ligand discrimination," Cell, 2017, 159:108-119.

Van den Berg et al., "Cellular-level versus receptor-level response threshold hierarchies in T-cell activation," Front. Immunol., 2013, 4:250.

Van der Stegen et al., "The pharmacology of second-generation chimeric antigen receptors," Nat. Rev. Drug Discov., 14: 499-509, 2015.

Vigano et al., "Functional avidity: a measure to predict the efficacy of effector T cells?" Clin. Dev. Immunol., 2012: 153863, 2012.

Viola & Lanzavecchia, "T cell activation determined by T cell receptor number and tunable thresholds," Science, 273: 104-106, 1996.

Wherry & Kurachi, "Molecular and cellular insights into T cell exhaustion," Nat. Rev. Immunol., 15: 486-499, 2015.

Wu et al., "Hepatocyte-directed Gene Transfer in Vivo Leads to Transient Improvement of Hypercholesterolemia in Low Density Lipoprotein Receptor-deficient Rabbits", J. Biol. Chem. 267: 963, 1992.

Wu et al., "Receptor-mediated Gene Delivery and Expression in Vivo", J. Biol. Chem. 263: 14621, 1988.

Wu et al., "Receptor-mediated in Vitro Gene Transformation by a Soluble DNA Carrier System", J. Biol. Chem. 262: 4429-4432, 1987.

Xiang et al., "Targeted activation of human Vgamma9Vdelta2-T cells controls epstein-barr virus-induced B cell lymphoproliferative disease," Cancer Cell, 26: 565-576, 2014.

Yang et al., "In vivo and in vitro gene transfer to mammalian somatic cells by particle bombardment", Proc. Natl. Acad. Sci., 87: 9568-9572, 1990.

Young et al., "Epstein-Barr virus: more than 50 years old and still providing surprises," Nat. Rev. Cancer, 16:789-802, 2016.

Yuan et al., "CTLA-4 blockade enhances polyfunctional NY-ESO-1 specific T cell responses in metastatic melanoma patients with clinical benefit," Proc. Natl. Acad. Sci. USA, 105: 20410-20415, 2008.

Zhang et al., "Epstein-Barr virus (EBV) latent membrane protein 1 increases HLA class II expression in an EBV-negative B cell line," Eur. J. Immunol., 24: 1467-1470, 1994.

* cited by examiner

Variable region of anti-MVR heavy chain
1) Nucleotide sequence
CAGGTGCAGCTGAAAGAGTCAGGACCTGGCCTGGTGGCACCCTCACAGAGCCTGT
CCATCACATGCACTGTCTCTGGGTTCTCATTATCCAGATATAGTGTACACTGGGT
TCGCCAGCCTCCAGGAAAGGGTCTGGAGTGGCTGGGAATGATATGGGGTGGTGGA
AGCACAGACTATAATTCAGCTCTCAAATCCAGACTGAGCATCAGCAAGGACAACT
CCAAGAGCCAAGTTTTCTTAAAAATGAACAGTCTGCAAACTGATGACACAGCCAT
GTACTACTGTGCCAGAAATGAGGGGGATACTACGGCTGGGACCTGGTTTGCTTAC
TGGGGCCAAGGGACTCTGGTCACTGTCTCTGCG
2) Amino acid sequence
QVQLKESGPGLVAPSQSLSITCTVSGFSLSRYSVHWVRQPPGKGLEWLGMIWGGG
STDYNSALKSRLSISKDNSKSQVFLKMNSLQTDDTAMYYCARNEGDTTAGTWFAY
WGQGTLVTVSA Variable region of anti-MVR light chain
1) Nucleotide sequence
GACATTCAGATGACCCAATCTTCATCCTACTTGTCTGTATCTCTAGGAGGCAGAG
TCACCATTACTTGCAAGGCAAGTGACCACATTAATAATTGGTTAGCCTGGTATCA
GCAGAAACCAGGAAATGCTCCTAGGCTCTTAATATCTGGTGCAACCAGTTTGGAA
ACTGGGGTTCCTTCAAGATTCAGTGGCAGTGGATCTGGAAAGGATTACACTCTCA
GCATTACCAGTCTTCAGACTGAAGATGTTGCTACTTATTACTGTCAACAGTATTG
GAGTACTCCATTCACGTTCGGCTCGGGGACAAAGTTGGAGATCAAA
2) Amino acid sequence
DIQMTQSSSYLSVSLGGRVTITCKASDHINNWLAWYQQKPGNAPRLLISGATSLE
TGVPSRFSGSGSGKDYTLSITSLQTEDVATYYCQQYWSTPFTFGSGTKLEIK CDR1 in red, CDR2 in blue, CDR3 in brown

FIG. 6

SEQUENCE LISTING

```
<160> NUMBER OF SEQ ID NOS: 59

<210> SEQ ID NO 1
<211> LENGTH: 121
<212> TYPE: PRT
<213> ORGANISM: Artificial Sequence
<220> FEATURE:
<223> OTHER INFORMATION: Variable region of anti-MVR heavy chain

<400> SEQUENCE: 1

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Arg Tyr
            20                  25                  30

Ser Val His Trp Val Arg Gln Pro Pro Gly Lys Gly Leu Glu Trp Leu
        35                  40                  45

Gly Met Ile Trp Gly Gly Gly Ser Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Thr Ala Met Tyr Tyr Cys Ala
                85                  90                  95

Arg Asn Glu Gly Asp Thr Thr Ala Gly Thr Trp Phe Ala Tyr Trp Gly
            100                 105                 110

Gln Gly Thr Leu Val Thr Val Ser Ala
        115                 120
```

```
115                 120

<210> SEQ ID NO 2
<211> LENGTH: 5
<212> TYPE: PRT
<213> ORGANISM: Artificial Sequence
<220> FEATURE:
<223> OTHER INFORMATION: CDR1 of anti-MVR heavy chain

<400> SEQUENCE: 2

Arg Tyr Ser Val His
1               5

<210> SEQ ID NO 3
<211> LENGTH: 16
<212> TYPE: PRT
<213> ORGANISM: Artificial Sequence
<220> FEATURE:
<223> OTHER INFORMATION: CDR2 of anti-MVR heavy chain

<400> SEQUENCE: 3

Met Ile Trp Gly Gly Gly Ser Thr Asp Tyr Asn Ser Ala Leu Lys Ser
1               5                  10                  15

<210> SEQ ID NO 4
<211> LENGTH: 17
<212> TYPE: PRT
<213> ORGANISM: Artificial Sequence
<220> FEATURE:
<223> OTHER INFORMATION: CDR3 of anti-MVR heavy chain

<400> SEQUENCE: 4

Cys Ala Arg Asn Glu Gly Asp Thr Thr Ala Gly Thr Trp Phe Ala Tyr
1               5                  10                  15

Trp

<210> SEQ ID NO 5
<211> LENGTH: 107
<212> TYPE: PRT
<213> ORGANISM: Artificial Sequence
<220> FEATURE:
<223> OTHER INFORMATION: Variable region of anti-MVR light chain

<400> SEQUENCE: 5

Asp Ile Gln Met Thr Gln Ser Ser Ser Tyr Leu Ser Val Ser Leu Gly
1               5                  10                  15

Gly Arg Val Thr Ile Thr Cys Lys Ala Ser Asp His Ile Asn Asn Trp
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Thr Pro Phe
                85                  90                  95

Thr Phe Gly Ser Gly Thr Lys Leu Glu Ile Lys
            100                 105

<210> SEQ ID NO 6
<211> LENGTH: 11
<212> TYPE: PRT
<213> ORGANISM: Artificial Sequence
```

```
<220> FEATURE:
<223> OTHER INFORMATION: CDR1 of anti-MVR light chain

<400> SEQUENCE: 6

Lys Ala Ser Asp His Ile Asn Asn Trp Leu Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: CDR2 of anti-MVR light chain

<400> SEQUENCE: 7

Gly Ala Thr Ser Leu Glu Thr
1               5

<210> SEQ ID NO 8
<211> LENGTH: 9
<212> TYPE: PRT
<213> ORGANISM: Artificial Sequence
<220> FEATURE:
<223> OTHER INFORMATION: CDR3 of anti-MVR light chain

<400> SEQUENCE: 8

Gln Gln Tyr Trp Ser Thr Pro Phe Thr
1               5

<210> SEQ ID NO 9
<211> LENGTH: 363
<212> TYPE: DNA
<213> ORGANISM: Artificial Sequence
<220> FEATURE:
<223> OTHER INFORMATION: Variable region of anti-MVR heavy chain

<400> SEQUENCE: 9
caggtgcagc tgaaagagtc aggacctggc ctggtggcac cctcacagag cctgtccatc      60
acatgcactg tctctgggtt ctcattatcc agatatagtg tacactgggt tcgccagcct     120
ccaggaaagg gtctggagtg gctgggaatg atatggggtg gtggaagcac agactataat     180
tcagctctca aatccagact gagcatcagc aaggacaact ccaagagcca agttttctta     240
aaaatgaaca gtctgcaaac tgatgacaca gccatgtact actgtgccag aaatgagggg     300
gatactacgg ctgggacctg gtttgcttac tggggccaag ggactctggt cactgtctct     360
gcg                                                                  363

<210> SEQ ID NO 10
<211> LENGTH: 15
<212> TYPE: DNA
<213> ORGANISM: Artificial Sequence
<220> FEATURE:
<223> OTHER INFORMATION: CDR1 of anti-MVR heavy chain

<400> SEQUENCE: 10
agatatagtg tacac                                                      15

<210> SEQ ID NO 11
<211> LENGTH: 48
<212> TYPE: DNA
<213> ORGANISM: Artificial Sequence
<220> FEATURE:
<223> OTHER INFORMATION: CDR2 of anit-MVR heavy chain

<400> SEQUENCE: 11
```

```
atgatatggg gtggtggaag cacagactat aattcagctc tcaaatcc          48
```

<210> SEQ ID NO 12
<211> LENGTH: 51
<212> TYPE: DNA
<213> ORGANISM: Artificial Sequence
<220> FEATURE:
<223> OTHER INFORMATION: CDR3 of anti-MVR heavy chain

<400> SEQUENCE: 12

```
tgtgccagaa atgaggggga tactacggct gggacctggt ttgcttactg g       51
```

<210> SEQ ID NO 13
<211> LENGTH: 321
<212> TYPE: DNA
<213> ORGANISM: Artificial Sequence
<220> FEATURE:
<223> OTHER INFORMATION: Variable region of anti-MVR light chain

<400> SEQUENCE: 13

```
gacattcaga tgacccaatc ttcatcctac ttgtctgtat ctctaggagg cagagtcacc    60
attacttgca aggcaagtga ccacattaat aattggttag cctggtatca gcagaaacca   120
ggaaatgctc ctaggctctt aatatctggt gcaaccagtt tggaaactgg ggttccttca   180
agattcagtg gcagtggatc tggaaaggat tacactctca gcattaccag tcttcagact   240
gaagatgttg ctacttatta ctgtcaacag tattggagta ctccattcac gttcggctcg   300
gggacaaagt tggagatcaa a                                             321
```

<210> SEQ ID NO 14
<211> LENGTH: 33
<212> TYPE: DNA
<213> ORGANISM: Artificial Sequence
<220> FEATURE:
<223> OTHER INFORMATION: CDR1 of anti-MVR light chain

<400> SEQUENCE: 14

```
aaggcaagtg accacattaa taattggtta gcc                          33
```

<210> SEQ ID NO 15
<211> LENGTH: 21
<212> TYPE: DNA
<213> ORGANISM: Artificial Sequence
<220> FEATURE:
<223> OTHER INFORMATION: CDR2 of anti-MVR light chain

<400> SEQUENCE: 15

```
ggtgcaacca gtttggaaac t                                       21
```

<210> SEQ ID NO 16
<211> LENGTH: 27
<212> TYPE: DNA
<213> ORGANISM: Artificial Sequence
<220> FEATURE:
<223> OTHER INFORMATION: CDR3 of anti-MVR light chain

<400> SEQUENCE: 16

```
caacagtatt ggagtactcc attcacg                                 27
```

<210> SEQ ID NO 17
<211> LENGTH: 25
<212> TYPE: RNA
<213> ORGANISM: Artificial Sequence
<220> FEATURE:

<223> OTHER INFORMATION: siRNA for CD74

<400> SEQUENCE: 17
gcaacaugac agaggaccau gugau                                      25

<210> SEQ ID NO 18
<211> LENGTH: 25
<212> TYPE: DNA
<213> ORGANISM: Artificial Sequence
<220> FEATURE:
<223> OTHER INFORMATION: Forward primer for CD74 p35 and p43

<400> SEQUENCE: 18
ctcgagatgc acaggagaag cagga                                      25

<210> SEQ ID NO 19
<211> LENGTH: 25
<212> TYPE: DNA
<213> ORGANISM: Artificial Sequence
<220> FEATURE:
<223> OTHER INFORMATION: Forward primer for CD74 p41

<400> SEQUENCE: 19
ctcgagatgg atgaccagcg cgacc                                      25

<210> SEQ ID NO 20
<211> LENGTH: 24
<212> TYPE: DNA
<213> ORGANISM: Artificial Sequence
<220> FEATURE:
<223> OTHER INFORMATION: Reverse primer for CD74 p35, p43 and p41

<400> SEQUENCE: 20
gaattctcac atggggactg ggcc                                       24

<210> SEQ ID NO 21
<211> LENGTH: 41
<212> TYPE: DNA
<213> ORGANISM: Artificial Sequence
<220> FEATURE:
<223> OTHER INFORMATION: MVK1

<400> SEQUENCE: 21
gctaccgtag cacaggcagc cgayatccag atgacacarw c                    41

<210> SEQ ID NO 22
<211> LENGTH: 41
<212> TYPE: DNA
<213> ORGANISM: Artificial Sequence
<220> FEATURE:
<223> OTHER INFORMATION: MVK2

<400> SEQUENCE: 22
gctaccgtag cacaggcagc cgaaawtgtg ctcacccagt c                    41

<210> SEQ ID NO 23
<211> LENGTH: 41
<212> TYPE: DNA
<213> ORGANISM: Artificial Sequence
<220> FEATURE:
<223> OTHER INFORMATION: MVK3

<400> SEQUENCE: 23
gctaccgtag cacaggcagc cgacattgtg ctracmcagt c                    41

```
<210> SEQ ID NO 24
<211> LENGTH: 41
<212> TYPE: DNA
<213> ORGANISM: Artificial Sequence
<220> FEATURE:
<223> OTHER INFORMATION: MVK4

<400> SEQUENCE: 24
gctaccgtag cacaggcagc cgacattgtg atgtcacagt c          41

<210> SEQ ID NO 25
<211> LENGTH: 41
<212> TYPE: DNA
<213> ORGANISM: Artificial Sequence
<220> FEATURE:
<223> OTHER INFORMATION: MVK5

<400> SEQUENCE: 25
gctaccgtag cacaggcagc cgatattgtg ctaactcagt c          41

<210> SEQ ID NO 26
<211> LENGTH: 41
<212> TYPE: DNA
<213> ORGANISM: Artificial Sequence
<220> FEATURE:
<223> OTHER INFORMATION: MVK6

<400> SEQUENCE: 26
gctaccgtag cacaggcagc cgacatcygg atgactcagt c          41

<210> SEQ ID NO 27
<211> LENGTH: 41
<212> TYPE: DNA
<213> ORGANISM: Artificial Sequence
<220> FEATURE:
<223> OTHER INFORMATION: MVK7

<400> SEQUENCE: 27
gctaccgtag cacaggcagc caacattgtr mtgacccaat c          41

<210> SEQ ID NO 28
<211> LENGTH: 41
<212> TYPE: DNA
<213> ORGANISM: Artificial Sequence
<220> FEATURE:
<223> OTHER INFORMATION: MVK8

<400> SEQUENCE: 28
gctaccgtag cacaggcagc cgacatycag atgachcagt c          41

<210> SEQ ID NO 29
<211> LENGTH: 41
<212> TYPE: DNA
<213> ORGANISM: Artificial Sequence
<220> FEATURE:
<223> OTHER INFORMATION: MVK9

<400> SEQUENCE: 29
gctaccgtag cacaggcagc cgaaacaact gtgacccagt c          41

<210> SEQ ID NO 30
<211> LENGTH: 41
<212> TYPE: DNA
<213> ORGANISM: Artificial Sequence
<220> FEATURE:
<223> OTHER INFORMATION: MVK10
```

```
<400> SEQUENCE: 30
gctaccgtag cacaggcagc cgacattgtg ctsacccaat c                    41

<210> SEQ ID NO 31
<211> LENGTH: 24
<212> TYPE: DNA
<213> ORGANISM: Artificial Sequence
<220> FEATURE:
<223> OTHER INFORMATION: MCK

<400> SEQUENCE: 31
gttgttcaag aagcacacga ctga                                       24

<210> SEQ ID NO 32
<211> LENGTH: 26
<212> TYPE: DNA
<213> ORGANISM: Artificial Sequence
<220> FEATURE:
<223> OTHER INFORMATION: MVH1

<400> SEQUENCE: 32
atggccgagg trmagcttca ggagtc                                     26

<210> SEQ ID NO 33
<211> LENGTH: 26
<212> TYPE: DNA
<213> ORGANISM: Artificial Sequence
<220> FEATURE:
<223> OTHER INFORMATION: MVH2

<400> SEQUENCE: 33
atggccgagg tbcagctbca gcagtc                                     26

<210> SEQ ID NO 34
<211> LENGTH: 26
<212> TYPE: DNA
<213> ORGANISM: Artificial Sequence
<220> FEATURE:
<223> OTHER INFORMATION: MVH3

<400> SEQUENCE: 34
atggccgagg tgcagctgaa gsastc                                     26

<210> SEQ ID NO 35
<211> LENGTH: 26
<212> TYPE: DNA
<213> ORGANISM: Artificial Sequence
<220> FEATURE:
<223> OTHER INFORMATION: MVH4

<400> SEQUENCE: 35
atggccgagg tccarctgca acartc                                     26

<210> SEQ ID NO 36
<211> LENGTH: 26
<212> TYPE: DNA
<213> ORGANISM: Artificial Sequence
<220> FEATURE:
<223> OTHER INFORMATION: MVH5

<400> SEQUENCE: 36
atggccgagg tycagctbca gcartc                                     26

<210> SEQ ID NO 37
<211> LENGTH: 26
```

<212> TYPE: DNA
<213> ORGANISM: Artificial Sequence
<220> FEATURE:
<223> OTHER INFORMATION: MVH6

<400> SEQUENCE: 37
atggccgagg tycarctgca gcagtc                                          26

<210> SEQ ID NO 38
<211> LENGTH: 26
<212> TYPE: DNA
<213> ORGANISM: Artificial Sequence
<220> FEATURE:
<223> OTHER INFORMATION: MVH7

<400> SEQUENCE: 38
atggccgagg tccacgtgaa gcagtc                                          26

<210> SEQ ID NO 39
<211> LENGTH: 26
<212> TYPE: DNA
<213> ORGANISM: Artificial Sequence
<220> FEATURE:
<223> OTHER INFORMATION: MVH8

<400> SEQUENCE: 39
atggccgagg tgaasstggt ggaatc                                          26

<210> SEQ ID NO 40
<211> LENGTH: 26
<212> TYPE: DNA
<213> ORGANISM: Artificial Sequence
<220> FEATURE:
<223> OTHER INFORMATION: MVH9

<400> SEQUENCE: 40
atggccgagg tgawgytggt ggagtc                                          26

<210> SEQ ID NO 41
<211> LENGTH: 26
<212> TYPE: DNA
<213> ORGANISM: Artificial Sequence
<220> FEATURE:
<223> OTHER INFORMATION: MVH10

<400> SEQUENCE: 41
atggccgagg tgcagskggt ggagtc                                          26

<210> SEQ ID NO 42
<211> LENGTH: 26
<212> TYPE: DNA
<213> ORGANISM: Artificial Sequence
<220> FEATURE:
<223> OTHER INFORMATION: MVH11

<400> SEQUENCE: 42
atggccgagg tgcamctggt ggagtc                                          26

<210> SEQ ID NO 43
<211> LENGTH: 26
<212> TYPE: DNA
<213> ORGANISM: Artificial Sequence
<220> FEATURE:
<223> OTHER INFORMATION: MVH12

<400> SEQUENCE: 43
atggccgagg tgaagctgat ggartc                                              26

<210> SEQ ID NO 44
<211> LENGTH: 26
<212> TYPE: DNA
<213> ORGANISM: Artificial Sequence
<220> FEATURE:
<223> OTHER INFORMATION: MVH13

<400> SEQUENCE: 44
atggccgagg tgcarcttgt tgagtc                                              26

<210> SEQ ID NO 45
<211> LENGTH: 26
<212> TYPE: DNA
<213> ORGANISM: Artificial Sequence
<220> FEATURE:
<223> OTHER INFORMATION: MVH14

<400> SEQUENCE: 45
atggccgagg traagcttct cgagtc                                              26

<210> SEQ ID NO 46
<211> LENGTH: 26
<212> TYPE: DNA
<213> ORGANISM: Artificial Sequence
<220> FEATURE:
<223> OTHER INFORMATION: MVH15

<400> SEQUENCE: 46
atggccgagg tgaarsttga ggagtc                                              26

<210> SEQ ID NO 47
<211> LENGTH: 28
<212> TYPE: DNA
<213> ORGANISM: Artificial Sequence
<220> FEATURE:
<223> OTHER INFORMATION: MVH16

<400> SEQUENCE: 47
atggccgagg ttactctraa agwgtstg                                            28

<210> SEQ ID NO 48
<211> LENGTH: 26
<212> TYPE: DNA
<213> ORGANISM: Artificial Sequence
<220> FEATURE:
<223> OTHER INFORMATION: MVH17

<400> SEQUENCE: 48
atggccgagg tccaactvca gcarcc                                              26

<210> SEQ ID NO 49
<211> LENGTH: 26
<212> TYPE: DNA
<213> ORGANISM: Artificial Sequence
<220> FEATURE:
<223> OTHER INFORMATION: MVH18

<400> SEQUENCE: 49
atggccgagg tgaacttgga agtgtc                                              26

<210> SEQ ID NO 50
<211> LENGTH: 26
<212> TYPE: DNA
<213> ORGANISM: Artificial Sequence

<220> FEATURE:
<223> OTHER INFORMATION: MVH19

<400> SEQUENCE: 50
atggccgagg tgaaggtcat cgagtc                                    26

<210> SEQ ID NO 51
<211> LENGTH: 23
<212> TYPE: DNA
<213> ORGANISM: Artificial Sequence
<220> FEATURE:
<223> OTHER INFORMATION: MVC

<400> SEQUENCE: 51
aggacagccg ggaaggtgtg cac                                       23

<210> SEQ ID NO 52
<211> LENGTH: 15
<212> TYPE: PRT
<213> ORGANISM: Artificial Sequence
<220> FEATURE:
<223> OTHER INFORMATION: (GLY4SER)3 linker

<400> SEQUENCE: 52

Gly Gly Gly Gly Ser Gly Gly Gly Gly Ser Gly Gly Gly Gly Ser
1               5                   10                  15

<210> SEQ ID NO 53
<211> LENGTH: 487
<212> TYPE: PRT
<213> ORGANISM: Artificial Sequence
<220> FEATURE:
<223> OTHER INFORMATION: CAR Protein

<400> SEQUENCE: 53

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Ser Ser Tyr Leu
                20                  25                  30

Ser Val Ser Leu Gly Gly Arg Val Thr Ile Thr Cys Lys Ala Ser Asp
        35                  40                  45

His Ile Asn Asn Trp Leu Ala Trp Tyr Gln Gln Lys Pro Gly Asn Ala
    50                  55                  60

Pro Arg Leu Leu Ile Ser Gly Ala Thr Ser Leu Glu Thr Gly Val Pro
65                  70                  75                  80

Ser Arg Phe Ser Gly Ser Gly Ser Gly Lys Asp Tyr Thr Leu Ser Ile
                85                  90                  95

Thr Ser Leu Gln Thr Glu Asp Val Ala Thr Tyr Tyr Cys Gln Gln Tyr
            100                 105                 110

Trp Ser Thr Pro Phe Thr Phe Gly Ser Gly Thr Lys Leu Glu Ile Lys
        115                 120                 125

Gly Gly Gly Gly Ser Gly Gly Gly Gly Ser Gly Gly Gly Gly Ser Gln
    130                 135                 140

Val Gln Leu Lys Glu Ser Gly Pro Gly Leu Val Ala Pro Ser Gln Ser
145                 150                 155                 160

Leu Ser Ile Thr Ser Thr Val Ser Gly Phe Ser Leu Ser Arg Tyr Ser
                165                 170                 175

Val His Trp Val Arg Gln Pro Pro Gly Lys Gly Leu Glu Trp Leu Gly
            180                 185                 190

Met Ile Trp Gly Gly Gly Ser Thr Asp Tyr Asn Ser Ala Leu Lys Ser

```
                195                 200                 205
Arg Leu Ser Ile Ser Lys Asp Asn Ser Lys Ser Gln Val Phe Leu Lys
        210                 215                 220

Met Asn Ser Leu Gln Thr Asp Asp Thr Ala Met Tyr Tyr Cys Ala Arg
225                 230                 235                 240

Asn Glu Gly Asp Thr Thr Ala Gly Thr Trp Phe Ala Tyr Trp Gly Gln
                245                 250                 255

Gly Thr Leu Val Thr Val Ser Ser Thr Thr Pro Ala Pro Arg Pro
        260                 265                 270

Pro Thr Pro Ala Pro Thr Ile Ala Ser Gln Pro Leu Ser Leu Arg Pro
                275                 280                 285

Glu Ala Cys Arg Pro Ala Ala Gly Gly Ala Val His Thr Arg Gly Leu
290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Lys Arg Gly
                325                 330                 335

Arg Lys Lys Leu Leu Tyr Ile Phe Lys Gln Pro Phe Met Arg Pro Val
                340                 345                 350

Gln Thr Thr Gln Glu Glu Asp Gly Cys Ser Cys Arg Phe Pro Glu Glu
        355                 360                 365

Glu Glu Gly Gly Cys Glu Leu Arg Val Lys Phe Ser Arg Ser Ala Asp
370                 375                 380

Ala Pro Ala Tyr Lys Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
                420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Arg Gly Lys Gly His Asp Gly Leu
450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 54
<211> LENGTH: 1467
<212> TYPE: DNA
<213> ORGANISM: Artificial Sequence
<220> FEATURE:
<223> OTHER INFORMATION: CAR protein

<400> SEQUENCE: 54 atggcttac cagtgaccgc cttgctcctg ccgctggcct tgctgctcca cgccgccagg     60
ccggacattc agatgaccca atcttcatcc tacttgtctg tatctctagg aggcagagtc    120
accattactt gcaaggcaag tgaccacatt aataattggt tagcctggta tcagcagaaa    180
ccaggaaatg ctcctaggct cttaatatct ggtgcaacca gtttggaaac tggggttcct    240
tcaagattca gtggcagtgg atctggaaag gattacactc tcagcattac cagtcttcag    300
actgaagatt ttgctactta ttactgtcaa cagtattgga gtactccatt cacgttcggc    360
tcggggacaa agttggagat caaaggcgga ggcggatctg gcggcggagg aagtggcgga    420
```

```
ggggatctc aggtgcagct gaaagagtca ggacctggcc tggtggcacc ctcacagagc    480
ctgtccatca catgcactgt ctctgggttc tcattatcca gatatagtgt acactgggtt    540
cgccagcctc caggaaaggg tctggagtgg ctgggaatga tatggggtgg tggaagcaca    600
gactataatt cagctctcaa atccagactg agcatcagca aggacaactc caagagccaa    660
gttttcttaa aaatgaacag tctgcaaact gatgacacag ccatgtacta ctgtgccaga    720
aatgagggg atactacggc tgggacctgg tttgcttact ggggccaagg gactctggtc    780
actgtctctg cgagcaccac gacgccagcg ccgcgaccac caacaccggc gcccaccatc    840
gcgtcgcagc cctgtccct gcgcccagag gcgtgccggc cagcggcggg gggcgcagtg    900
cacacgaggg ggctggactt cgcctgtgat atctacatct gggcgccctt ggccgggact    960
tgtggggtcc ttctcctgtc actggttatc acccttact gcaaacgggg cagaaagaaa    1020
ctcctgtata tattcaaaca accatttatg agaccagtac aaactactca agaggaagat    1080
ggctgtagct gccgatttcc agaagaagaa gaaggaggat gtgaactgag agtgaagttc    1140
agcaggagcg cagacgcccc cgcgtacaag cagggccaga accagctcta taacgagctc    1200
aatctaggac gaagagagga gtacgatgtt ttggacaaga cgtggccg ggaccctgag    1260
atgggggaa agccgagaag gaagaaccct caggaaggcc tgtacaatga actgcagaaa    1320
gataagatgg cggaggccta cagtgagatt gggatgaaag cgagcgccg gaggggcaag    1380
gggcacgatg ccttttacca gggtctcagt acagccacca aggacaccta cgacgccctt    1440
cacatgcagg ccctgccccc tcgctaa                                       1467
```

<210> SEQ ID NO 55
<211> LENGTH: 21
<212> TYPE: PRT
<213> ORGANISM: Artificial Sequence
<220> FEATURE:
<223> OTHER INFORMATION: CD8 alpha leader sequence

<400> SEQUENCE: 55

Met Ala Leu Pro Val Thr Ala Leu Leu Leu Pro Leu Ala Leu Leu Leu
1               5                   10                  15

His Ala Ala Arg Pro
            20

<210> SEQ ID NO 56
<211> LENGTH: 243
<212> TYPE: PRT
<213> ORGANISM: Artificial Sequence
<220> FEATURE:
<223> OTHER INFORMATION: anti-MVR VL and GlySer linker and anti-MVR VH

<400> SEQUENCE: 56

Asp Ile Gln Met Thr Gln Ser Ser Ser Tyr Leu Ser Val Ser Leu Gly
1               5                   10                  15

Gly Arg Val Thr Ile Thr Cys Lys Ala Ser Asp His Ile Asn Asn Trp
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Thr Pro Phe

```
                    85                  90                  95
Thr Phe Gly Ser Gly Thr Lys Leu Glu Ile Lys Gly Gly Gly Ser
                100                 105                 110
Gly Gly Gly Gly Ser Gly Gly Gly Ser Gln Val Gln Leu Lys Glu
                115                 120                 125
Ser Gly Pro Gly Leu Val Ala Pro Ser Gln Ser Leu Ser Ile Thr Cys
            130                 135                 140
Thr Val Ser Gly Phe Ser Leu Ser Arg Tyr Ser Val His Trp Val Arg
145                 150                 155                 160
Gln Pro Pro Gly Lys Gly Leu Glu Trp Leu Gly Met Ile Trp Gly Gly
                165                 170                 175
Gly Ser Thr Asp Tyr Asn Ser Ala Leu Lys Ser Arg Leu Ser Ile Ser
                180                 185                 190
Lys Asp Asn Ser Leu Ser Gln Val Phe Leu Lys Met Asn Ser Leu Gln
                195                 200                 205
Thr Asp Asp Thr Ala Met Tyr Tyr Cys Ala Arg Asn Glu Gly Asp Thr
            210                 215                 220
Thr Ala Gly Thr Trp Phe Ala Tyr Trp Gly Gln Gly Thr Leu Val Thr
225                 230                 235                 240
Val Ser Ser

<210> SEQ ID NO 57
<211> LENGTH: 243
<212> TYPE: PRT
<213> ORGANISM: Artificial Sequence
<220> FEATURE:
<223> OTHER INFORMATION: CD8 alpha spanning from hinge region to
      transmembrane region

<400> SEQUENCE: 57

Asp Ile Gln Met Thr Gln Ser Ser Tyr Leu Ser Val Ser Leu Gly
1               5                   10                  15
Gly Arg Val Thr Ile Thr Cys Lys Ala Ser Asp His Ile Asn Asn Trp
                20                  25                  30
Leu Ala Trp Tyr Gln Gln Lys Pro Gly Asn Ala Pro Arg Leu Leu Ile
            35                  40                  45
Ser Gly Ala Thr Ser Leu Glu Thr Gly Val Pro Ser Arg Phe Ser Gly
        50                  55                  60
Ser Gly Ser Gly Lys Asp Tyr Thr Leu Ser Ile Thr Ser Leu Gln Thr
65              70                  75                  80
Glu Asp Val Ala Thr Tyr Tyr Cys Gln Gln Tyr Trp Ser Thr Pro Phe
                85                  90                  95
Thr Phe Gly Ser Gly Thr Lys Leu Glu Ile Lys Gly Gly Gly Ser
                100                 105                 110
Gly Gly Gly Gly Ser Gly Gly Gly Ser Gln Val Gln Leu Lys Glu
                115                 120                 125
Ser Gly Pro Gly Leu Val Ala Pro Ser Gln Ser Leu Ser Ile Thr Ser
            130                 135                 140
Thr Val Ser Gly Phe Ser Leu Ser Arg Tyr Ser Val His Trp Val Arg
145                 150                 155                 160
Gln Pro Pro Gly Lys Gly Leu Glu Trp Leu Gly Met Ile Trp Gly Gly
                165                 170                 175
Gly Ser Thr Asp Tyr Asn Ser Ala Leu Lys Ser Arg Leu Ser Ile Ser
                180                 185                 190
Lys Asp Asn Ser Lys Ser Gln Val Phe Leu Lys Met Asn Ser Leu Gln
```

-continued

```
                195                 200                 205
Thr Asp Asp Thr Ala Met Tyr Tyr Cys Ala Arg Asn Glu Gly Asp Thr
    210                 215                 220
Thr Ala Gly Thr Trp Phe Ala Tyr Trp Gly Gln Gly Thr Leu Val Thr
225                 230                 235                 240
Val Ser Ser

<210> SEQ ID NO 58
<211> LENGTH: 42
<212> TYPE: PRT
<213> ORGANISM: Artificial Sequence
<220> FEATURE:
<223> OTHER INFORMATION: 4-1BB signaling domain

<400> SEQUENCE: 58

Lys Arg Gly Arg Lys Lys Leu Leu Tyr Ile Phe Lys Gln Pro Phe Met
1               5                   10                  15
Arg Pro Val Gln Thr Thr Gln Glu Glu Asp Gly Cys Ser Cys Arg Phe
            20                  25                  30
Pro Glu Glu Glu Glu Gly Gly Tyr Glu Leu
        35                  40

<210> SEQ ID NO 59
<211> LENGTH: 112
<212> TYPE: PRT
<213> ORGANISM: Artificial Sequence
<220> FEATURE:
<223> OTHER INFORMATION: TCR zeta signaling domain

<400> SEQUENCE: 59

Arg Val Lys Phe Ser Arg Ser Ala Asp Ala Pro Ala Tyr Lys Gln Gly
1               5                   10                  15
Gln Asn Gln Leu Tyr Asn Glu Leu Asn Leu Gly Arg Arg Glu Glu Tyr
            20                  25                  30
Asp Val Leu Asp Lys Arg Arg Gly Arg Asp Pro Glu Met Gly Gly Lys
        35                  40                  45
Pro Arg Arg Lys Asn Pro Gln Glu Gly Leu Tyr Asn Glu Leu Gln Lys
    50                  55                  60
Asp Lys Met Ala Glu Ala Tyr Ser Glu Ile Gly Met Lys Gly Glu Arg
65                  70                  75                  80
Arg Arg Gly Lys Gly His Asp Gly Leu Tyr Gln Gly Leu Ser Thr Ala
                85                  90                  95
Thr Lys Asp Thr Tyr Asp Ala Leu His Met Gln Ala Leu Pro Pro Arg
            100                 105                 110
```

MONOCLONAL ANTIBODY WHICH SPECIFICALLY RECOGNIZES B CELL LYMPHOMA AND USE THEREOF

CROSS-REFERENCE TO RELATED APPLICATIONS

This application is a Continuation of U.S. application Ser. No. 15/829,048, filed Dec. 21, 2017, which is a Divisional of U.S. application Ser. No. 14/639,679, filed Mar. 5, 2015, which claims priority under 35 U.S.C. § 119 of Korean Patent Application No. 10-2014-0026252, filed on Mar. 5, 2014. The entire contents of the foregoing are hereby incorporated by reference.

STATEMENT REGARDING SEQUENCE LISTING

The Sequence Listing associated with this application is provided in text form in lieu of a paper copy, and is hereby incorporated by reference into the specification. The name of the text file containing the Sequence Listing is Sequence-Listing.txt. The text file is 24.9 KB, and was created and submitted electronically via EFS-Web on Aug. 26, 2019.

BACKGROUND OF THE INVENTION

The present invention disclosed herein relates to a monoclonal antibody which specifically recognizing B cell lymphoma cell and a use thereof. More specifically, the present invention relates to a monoclonal antibody; a pharmaceutical composition for preventing or treating B cell lymphoma, including the monoclonal antibody; a composition for diagnosing B cell lymphoma including the monoclonal antibody; a method for providing information for diagnosing B cell lymphoma using the monoclonal antibody; a chimeric antigen receptor (CAR) protein including i) the antibody, ii) a transmembrane domain, and iii) an intracellular signaling domain; a recombinant vector which expresses the CAR protein; a CAR-modified T cell transformed with the recombinant vector; a pharmaceutical composition for preventing or treating B cell lymphoma including the CAR-modified T cell; and an antibody-drug conjugate in which the monoclonal antibody and a drug are conjugated.

B cell lymphoma consists of Hodgkin lymphoma (HL) and non-Hodgkin lymphoma (NHL). NHL is blood cancer which most frequently occurs in adults. NHL occurred in more than 66,000 people in the U.S. in 2008 and the annual occurrence rate is increased by 4%. Additionally, the occurrence of lymphoma is steadily increasing while those of some other cancers are decreasing.

Most of lymphoma/leukemia occurring from B cells expresses CD19 and CD20 on the cell surface, and therefore, based on this, a monoclonal antibody which recognizes CD20 has been developed as a therapeutic agent for treating B cell lymphoma/leukemia. Anti-CD20 monoclonal antibodies remove cancer through various mechanisms such as complement-dependent cytotoxicity (CDC), antibody-dependent cellular cytotoxicity (ADCC), and induction of apoptosis. The anti-CD20 monoclonal antibody (rituximab), which was approved by USFDA as a treatment for B cell NHL in 1977, has been used since then as a standard therapeutic method for treating diffused large B cell lymphoma (DLBCL) and other B cell lymphoma/leukemia in such a manner that it was administered in combination with cyclophosphamide plus doxorubicin, vincristine, prednisone (CHOP). However, malignant B cells and rituximab, regardless of their high reactivity, have a low effect of complete cure of less than 10%. This phenomenon is because some of B cell lymphoma/leukemia cells reduce CD20 expression thereby evading the action of rituximab. Additionally, there is a limitation that normal B cells also express CD20 and thus normal B cells are also removed by rituximab. In this regard, those cancer patients administered with rituximab are removed of humoral immunities and thus there is a high possibility of occurrence of side effects such as occurrence of type B hepatitis, increase of viral infections, and multifocal leukoencephalopathy. Accordingly, there has been a demand for the development of a next generation monoclonal antibody which selectively binds to B cell lymphoma/leukemia cells.

Under these circumstances, the present inventors have eagerly endeavored to develop a monoclonal antibody which selectively recognizes only malignant B cells, resultantly, have produced a pool of hybridomas which react with B cell lymphoma, and subsequently have succeeded to develop a hybridoma and antibodies produced therefrom, wherein the hybridoma has an anticancer activity and does not recognize cancer cells other than normal B cells and B cell lymphoma but selectively recognizes B cell lymphoma when subjected to a few steps of screening through flow cytometry analysis. Additionally, the present inventors confirmed that the above antibody has excellent anticancer activity both in vitro and in vivo against B cell lymphoma, and that the antibody exhibits excellent anticancer activity when the antibody is used as a therapeutic agent for chimeric antigen receptor (CAR)-T cells. Consequently, the present inventors confirmed that the antibody can be used in various forms of anticancer treatments such as an antibody-/anticancer-therapeutic agent containing the antibody as a major effect of ADCC mechanism, antibody therapeutic agent such as radioisotopes/anticancer agents/toxins, etc., which are in a form being bound to anticancer substances, and CAR-T cell treatment using scFv. Finally, the present inventors completed the present invention.

SUMMARY OF THE INVENTION

An object of the present invention is to provide a monoclonal antibody specific to B cell lymphoma, including: a heavy chain variable region having a heavy chain CDR1 described in SEQ ID NO: 2; a heavy chain CDR2 described in SEQ ID NO: 3; and a heavy chain CDR3 described in SEQ ID NO: 4; and a light chain variable region having a light chain CDR1 described in SEQ ID NO: 6; a light chain CDR2 described in SEQ ID NO: 7; and a light chain CDR3 described in SEQ ID NO: 8.

Another object of the present invention is to provide a pharmaceutical composition for preventing or treating B cell lymphoma containing the monoclonal antibody.

Still another object of the present invention is to provide a method for treating B cell lymphoma including administering the monoclonal antibody to a subject suspected of having B cell lymphoma.

Still another object of the present invention is to provide a composition for diagnosing B cell lymphoma containing the monoclonal antibody.

Still another object of the present invention is to provide a method of providing information for diagnosing B cell lymphoma including: (a) treating, with the monoclonal antibody, a separated biological sample from a subject suspected of having B cell lymphoma; and (b) detecting the presence of B cell lymphoma cells from the sample in step (a).

Still another object of the present invention is to provide a chimeric antigen receptor (CAR) protein, including: i) an antibody specific to B cell lymphoma; ii) a transmembrane domain; and iii) an intracellular signaling domain, which leads to T cell activation when an antigen binds to the antibody.

Still another object of the present invention is to provide a CAR-modified T cell transformed by a recombinant vector expressing the CAR protein.

Still another object of the present invention is to provide a pharmaceutical composition for preventing or treating B cell lymphoma containing the CAR-modified T cell.

Still another object of the present invention is to provide an antibody-drug conjugate wherein the monoclonal antibody and a drug are conjugated.

In an aspect to achieve the above objects, the present invention provides a monoclonal antibody specific to B cell lymphoma, including: a heavy chain variable region having a heavy chain CDR1 described in SEQ ID NO: 2; a heavy chain CDR2 described in SEQ ID NO: 3; and a heavy chain CDR3 described in SEQ ID NO: 4; and a light chain variable region having a light chain CDR1 described in SEQ ID NO: 6; a light chain CDR2 described in SEQ ID NO: 7; and a light chain CDR3 described in SEQ ID NO: 8.

The term "antibody" used herein refers to a protein molecule, which includes an immunoglobulin molecule having a reactivity with a specific antigen immunologically and acts as a receptor capable of specifically recognizing antigens. Examples of the antibody include all of polyclonal antibodies, monoclonal antibodies, full length antibodies and antibody fragments. Additionally, said term also refers to antibodies, humanized antibodies, bivalent or bispecific molecules (e.g., bispecific antibodies), diabodies, triabodies, and tetrabodies, but is not limited thereto. A full length refers to a structure having two full length light chains and two full length heavy chains, wherein each light chain is connected to a heavy chain by a disulfide bond. The full length antibody includes IgA, IgD, IgE, IgM and IgG, and IgG that includes as its subtypes $IgG_1$, $IgG_2$, $IgG_3$, and $IgG_4$. The antibody fragment refers to a fragment having a function capable of binding to antigens, and includes Fab, Fab', $F(ab')_2$, Fv, etc. The Fab has a structure including variable regions of the light chain and the heavy chain, a constant region of the light chain, and a first constant region (CH1 domain) of the heavy chain, and has one antigen binding site. Fab' differs from Fab in that Fab' has a hinge region, which includes at least one cysteine residue at the C-terminus of the heavy chain CH1 domain. $F(ab')_2$ antibody is produced as the cysteine residue in the hinge region of Fab' forms a disulfide bond. A variable fragment (Fv) refers to a minimum fragment having only a heavy chain variable region and a light chain variable region. The double chain Fv (dsFv) is characterized in that the heavy chain Fv (dsFv) is connected to the heavy chain variable region by a disulfide bond, whereas a single chain Fv (scFv) is generally characterized in that the heavy chain variable region and the light chain variable region are connected by a covalent bond through a peptide linker. The antibody fragment can be obtained using a protease (for example, Fab can be obtained by restriction digestion of full length antibodies with papain, and $F(ab')_2$ fragment can be obtained by cutting with pepsin), and preferably, may be constructed via genetic recombinant technology.

The term "monoclonal antibody" used herein refers to an antibody molecule having a single molecular composition obtained from a substantially identical antibody population, and the monoclonal antibody indicates a single binding specificity and affinity to a particular epitope.

Typically, an immunoglobulin has a heavy chain and a light chain, and each of the heavy chain and the light chain includes a constant region and a variable region (the region is also known as domain). The variable regions of the light chain and the heavy chain include three hypervariable regions called complementarity-determining region (hereinafter, "CDR") and four framework regions. The CDR mostly plays a role in binding to an epitope of an antigen. The CDR of each chain is typically called sequentially starting from the N-terminus CDR1, CDR2, and CDR3, and is identified by a chain to which a particular CDR is located.

When mouse monoclonal antibodies are repeatedly injected into the human body, they cause immune responses in the body and are thus difficult to be used as a therapeutic agent. Accordingly, in order to use the antibody of the present invention as a therapeutic antibody, it is preferable that the antibody be used in the form of a chimeric antibody, and more preferably in the form of a humanized antibody.

The term "chimeric antibody" used herein refers to a recombinant antibody between the variable region of a mouse antibody and the constant region of human antibody, and it shows a significant improvement in immune responses compared with that of the mouse antibody.

The term "humanized antibody" used herein refers to an antibody where the protein sequence of an antibody derived from a species other than humans is modified to be similar to that of an antibody mutant naturally produced in humans. For example, the humanized antibody may be prepared by preparing a humanized variable region by recombination between a mouse derived CDR and an FR derived from human antibody, followed by recombination between the humanized variable region and the preferable constant region of the human antibody. However, a simple CDR grafting would deteriorate the affinity of the humanized antibody. The affinity of the humanized antibody may be improved to a level equal to that of the original mouse antibody by rendering affinity on a few important FR amino acid residues that may affect the 3-dimensional structure of CDR to that of the mouse antibody, but is not limited thereto.

The term "B cell lymphoma-specific monoclonal antibody" used herein refers to an antibody which specifically recognizes B cell lymphoma cells, and according to the purpose of the present invention, refers to a monoclonal antibody which specifically recognizes a protein having a molecular weight of about 41 kDa located on the cell membrane of the B cell lymphoma cells, not normal B cells.

Preferably, the monoclonal antibody may be a monoclonal antibody including a heavy chain variable region having a heavy chain CDR1 described in SEQ ID NO: 2; a heavy chain CDR2 described in SEQ ID NO: 3; and a heavy chain CDR3 described in SEQ ID NO: 4; and a light chain variable region having a light chain CDR1 described in SEQ ID NO: 6; a light chain CDR2 described in SEQ ID NO: 7; and a light chain CDR3 described in SEQ ID NO: 8. More preferably, the monoclonal antibody may be a monoclonal antibody including an amino acid sequence of the heavy chain variable region described in SEQ ID NO: 1 and an amino acid sequence of the light chain variable region described in SEQ ID NO: 5, but is not limited thereto. In an exemplary embodiment of the present invention, the monoclonal antibody including an amino acid sequence of the heavy chain variable region described in SEQ ID NO: 1 and an amino acid sequence of the light chain variable region described in SEQ ID NO: 5 was designated as an anti-MVR (malignancy variant receptor) antibody.

Herein, the form of the monoclonal antibody may include, as stated above, both the full length antibodies and antibody fragments, and may be in any form such as a mouse monoclonal antibody, a chimeric antibody, and a humanized antibody.

Additionally, when the monoclonal antibody includes the heavy chain constant region, it may include a heavy chain constant region selected from the group consisting of human IgG1, IgG2, IgG3, IgG4, IgA, IgE, IgM, and IgD, and preferably, a human $IgG_1$ constant region, but is not limited thereto.

Since the monoclonal antibody acts specifically upon B cell lymphoma by recognizing the proteins specifically present in B cell lymphoma, it may be used as an antibody for diagnosing and treating B cell lymphoma.

The term "B cell lymphoma" used herein refers to a malignant lymphoma of B cell origin. The lymphoma includes Hodgkin's lymphoma and non-Hodgkin's lymphoma. Additionally, B cell lymphoma includes diffuse large B cell lymphoma (DLBCL), follicular lymphoma, mucosa-associated lymphatic tissue lymphoma (MALT), chronic lymphocytic leukemia, mantle cell lymphoma (MCL), burkitt lymphoma, mediastinal large B cell lymphoma, waldenstrom macroglobulinemia, nodal marginal zone B cell lymphoma (NMZL), splenic marginal zone lymphoma (SMZL), intravascular large B-cell lymphoma, primary effusion lymphoma, lymphomatoid granulomatosis, and AIDS-related lymphoma, but is not particularly limited thereto as long as it is lymphoma of B cell origin.

In an embodiment of the present invention, a hybridoma pool was constructed by separating spleen cells from a Balb/c mouse subjected to repeated immune injections of B cell lymphoma cells of human origin, followed by fusion with SP2/0 myeloma cells, and after a few selection processes, those anti-MVR hybridomas which specifically reacted only with B cell lymphoma and showed high reactivity were selected from the hybridoma pool (Experimental Example 1). Additionally, it was confirmed that the anti-MVR monoclonal antibodies, which are produced by the above hybridoma, were specifically bound not only to B cell lymphoma cell lines but also to cancer cells of clinical cancer patients of B cell lymphoma/leukemia (Experimental Example 3). Also, a total antibody of chimeric anti-MVR (chiMVR mAb), where the variable region of the anti-MVR monoclonal antibody was conjugated to the constant region of human $IgG_1$, was constructed, and it was confirmed that the antibody showed an antibody-dependent cellular cytotoxicity (ADCC) in B cell lymphoma cells (Experimental Example 4 and 5). Additionally, when an immune-deficient $RAG2^{-/-}$ $c^{-/-}$ mouse was subcutaneously injected with LCL cancer cells on its back, intraperitoneally administered with the anti-MVR antibodies, and observed the lymph node metastasis, it was confirmed that the antibodies inhibited the lymph node metastasis of the LCL cells and selectively bound to the cancer cells (Experimental Example 6). The above results support that the monoclonal antibody of the present invention can specifically bind to B cell lymphoma and be used for diagnosis and treatment of B cell lymphoma.

In another aspect, the present invention provides a polynucleotide encoding the monoclonal antibody, a vector expressing the polynucleotide, and a transformant where the vector is introduced.

The monoclonal antibody is the same as explained above.

The expression vector including the polynucleotide encoding the monoclonal antibody provided in the present invention may be, although not particularly limited thereto, a vector capable of replicating and/or expressing the polynucleotide in a eukaryotic or prokaryotic cell including a mammalian cell (e.g., human-, monkey-, rabbit-, rat-, hamster-, mouse cell, etc.) a plant cell, a yeast cell, an insect cell, or a bacteria cell (e.g., E. coli, etc.), and preferably, may be operably connected to a suitable promoter so that the polynucleotide can be expressed in a host cell, and may be a vector including at least one selection marker. For example, it may be in the form where the polynucleotide is introduced into a phage, a plasmid, a cosmid, a mini-chromosome, a virus or retrovirus, etc.

The expression vector including the polynucleotide encoding the monoclonal antibody may be an expression vector which respectively includes the polynucleotide encoding the heavy chain or the light chain of the monoclonal antibody, or an expression vector which includes both polynucleotides encoding the heavy chain and the light chain of the monoclonal antibody.

The transformant introduced with the expression vector, provided in the present invention, may be, although not particularly limited thereto, transformed bacteria cells such as E. coli and Streptomyces, Salmonella typhimurium; yeast cells, fungal cells such as Pichia pasteris, etc.; insect cells such as Drosophila, Spodoptera Sf9 cells, etc.; animal cells such as Chinese hamster ovary (CHO) cells, SP2/0 (mouse myeloma), human lymphoblastoid, COS, NSO (mouse myeloma), 293T, bow melanoma cells, HT-1080, baby hamster kidney (BHK) cells, human embryonic kidney (HEK) cells, PERC.6 (human retina cells); or plant cells.

The term "introduction" used herein refers to a method for delivering a vector including the polynucleotide encoding the monoclonal antibody to a host cell. The introduction may be performed by various methods known in the art such as calcium phosphate-DNA co-precipitation, DEAE-dextran-mediated transfection, polybrene-mediated transfection, electroporation, microinjection, liposome fusion, lipofectamine, and protoplast fusion. Additionally, transduction refers to delivery of a target material inside a cell using a virus particle via infection. Additionally, the vector may be introduced into a host cell via gene bombardment, etc. In the present invention, introduction may be interchangeably used with transfection.

In another aspect, the present invention provides a pharmaceutical composition for preventing or treating B cell lymphoma containing the monoclonal antibody.

The monoclonal antibody and B cell lymphoma are the same as explained above.

The monoclonal antibody of the present invention does not act on different lymphomas or normal cells but it does only specifically recognize B cell lymphoma and thus exhibit anticancer activity on B cell lymphoma while minimizing its effect on normal cells and other kinds of cancer cells. Accordingly, the pharmaceutical composition can be effectively used for preventing or treating B cell lymphoma.

The term "prevention" used herein refers to all kinds of activities to inhibit or delay the occurrence of B cell lymphoma by the administration of the above composition, and the term "treatment" used herein refers to all kinds of activities to improve or advantageously change the symptoms of B cell lymphoma by the administration of the above composition.

The pharmaceutical composition may further contain a pharmaceutically acceptable carrier.

The term "pharmaceutically acceptable carrier" used herein refers to a carrier or diluents which neither stimulate a bio-organism nor inhibit the biological activity and characteristics of a compound to be administered. As the pharmaceutically acceptable carrier in the composition to be formulated into a liquid phase solution, saline, sterile water, ringer solution, buffered saline, albumin injection solution, dextrose solution, malto dextrin solution, glycerol, ethanol, or a combination of at least one component thereof may be used, and other additives such as an antioxidant, a buffer solution, and a bacteriostatic agent may be further added, as necessary. Additionally, the composition may be formulated into an injection formulation such as an aqueous solution, a suspension, an emulsion, a pill, a capsule, granule or a tablet by further adding a diluents, a dispersant, a surfactant, a binder, and a lubricant.

The pharmaceutical composition may be in various oral or parenteral formulations. For formulations, a commonly used filler, extender, binder, wetting agent, disintegrant, diluent such as a surfactant or excipient may be added. Solid formulations for oral administration may include tablets, pills, powders, granules, capsules, etc., and the solid formulations may be prepared by mixing at least one compound with at least one excipient, e.g., starch, sucrose or lactose, gelatin, etc. Additionally, lubricants such as magnesium stearate and talc may be used in addition to simple excipients. Examples of the liquid phase formulations for oral administration include suspensions, liquid medicines for internal use, emulsions, syrups, etc., and various excipients such as wetting agents, sweeteners, fragrant, preservatives, etc., may be included in addition to the simple diluents such as water and liquid paraffin. Examples of formulations for parenteral administration include sterile aqueous solutions, non-aqueous solvents, suspensions, emulsions, lyophilized formulations, and suppositories. Examples of the non-aqueous solvents and suspensions may include propylene glycol, polyethylene glycol, a vegetable oil such as olive oil, an injectable sterol such as ethyl oleate. Examples of the base for suppositories may include witepsol, macrogol, tween 61, cacao butter, laurinum, glycerogelatin, etc.

The pharmaceutical composition may be prepared in any formulation type selected from the group consisting of tablets, pills, powders, granules, capsules, suspensions, liquid medicines for internal use, emulsions, syrups, sterile aqueous solutions, non-aqueous solvents, lyophilized formulations, and suppositories.

The pharmaceutical composition of the present invention may be administered in a pharmaceutically effective amount.

The term "pharmaceutically effective amount" used herein refers to an amount sufficient for the treatment of a disease at a reasonable benefit/risk ratio applicable to a medical treatment, and the level of the effective dose may be determined according to factors including type of a subject, severity of illness, age, sex, drug activity, drug sensitivity of a subject, administration time, administration route and dissolution rate, length of treatment of the pharmaceutical composition of the present invention, drug(s) used simultaneously with the pharmaceutical composition of the present invention, and other factors well known in the medical field. The pharmaceutical composition of the present invention may be administered as an individual therapeutic agent or in combination with other therapeutic agent(s), and also sequentially or simultaneously with the conventional therapeutic agent(s). Additionally, it is important that an amount which can achieve the maximum effect with the least amount without any side effects be administered in consideration of all the factors described above.

In an embodiment of the present invention, it was confirmed that the anti-MVR monoclonal antibody of the present invention specifically bound to B cell lymphoma and exhibited an anticancer activity by acting on B cell lymphoma (Experimental Examples 1 to 5).

In another aspect, the present invention provides a method for treating B cell lymphoma including administering the monoclonal antibody to a subject suspected of having B cell lymphoma.

The monoclonal antibody, B cell lymphoma, and its treatment are the same as explained above.

The method for treating cancer may be a method for treating B cell lymphoma including administering a pharmaceutical composition containing the monoclonal antibody and additionally a pharmaceutically acceptable carrier to a subject having B cell lymphoma or suspected of having B cell lymphoma, and the pharmaceutically acceptable carrier is the same as explained above. Preferably, the method for treating B cell lymphoma is a method for treating B cell lymphoma including administering a composition containing the monoclonal antibody to a subject having B cell lymphoma.

The subject may include mammals such as cattle, pigs, sheep, chicken, dogs, and humans, birds, etc., and may be any subject, without limitation, whose cancer can be treated by administering the composition.

In particular, the composition may be administered in a pharmaceutically effective amount at a single or a multiple dose. More particularly, the composition may be administered in the form of a liquid formulation, powder formulation, an aerosol, a capsule formulation, an enteric-coated tablet or capsule or suppository formulation. The administration route may include intraperitoneal administration, intravenous administration, intramuscular administration, subcutaneous administration, intracutaneous administration, oral administration, topical administration, intranasal administration, intrapulmonary administration, and intrarectal administration, but is not limited thereto. However, because peptides are digested when orally treated, the composition for oral administration should be formulated such that the active drug be coated or protected from decomposition in the stomach. Additionally, a pharmaceutical composition may be administered using a random device which enables to move an active substance to a target cell.

In another aspect, the present invention provides a method of providing information for diagnosing B cell lymphoma including: (a) treating, with the monoclonal antibody, a separated biological sample from a subject suspected of having B cell lymphoma; and (b) detecting the presence of B cell lymphoma cells from the sample in step (a).

The monoclonal antibody and B cell lymphoma are the same as explained above. The method of providing information for diagnosing B cell lymphoma may enable to provide information for the diagnosis of B cell lymphoma by reacting the B cell lymphoma-specific monoclonal antibody of the present invention with a separated biological sample of a subject suspected of having B cell lymphoma, followed by confirming the presence of B cell lymphoma cells. Since the B cell lymphoma-specific monoclonal antibody does not react with normal cells or tissues, B cell lymphoma may be diagnosed by examining the number of B cell lymphoma cells bound to the monoclonal antibody, or the degree of antigen binding, and then comparing the amount with that of control group such as normal cells or tissues, but is not limited thereto.

The term "biological sample" used herein may include tissues, cells, whole blood, blood serum, blood plasma, histological autopsy sample (brain, skin, lymph node, spinal cord, etc.), cell culture supernatant, disrupted eukaryotic cells and bacteria expression system, etc., and preferably a blood sample such as whole blood, blood serum, and blood plasma, but is not limited thereto. The presence of B cell lymphoma may be detected by reacting the biological samples in a manipulated or unmanipulated state with the antibody of the present invention.

In particular, the monoclonal antibody may have a detection label. When the monoclonal antibody does not have a detection label, the detection may be performed using other antibodies which can capture the monoclonal antibody and have a detection label, but is not limited thereto.

In another aspect, the present invention provides a composition for diagnosing B cell lymphoma containing the monoclonal antibody.

The monoclonal antibody and B cell lymphoma are the same as explained above.

Since the monoclonal antibody of the present invention can specifically recognize B cell lymphoma, it may be used for the diagnosis of B cell lymphoma by detecting the presence of B cell lymphoma in a separated biological sample using the same.

In another aspect, the present invention provides a chimeric antigen receptor (CAR) protein, including: i) an antibody including a heavy chain variable region having a heavy chain CDR1 described in SEQ ID NO: 2; a heavy chain CDR2 described in SEQ ID NO: 3; and a heavy chain CDR3 described in SEQ ID NO: 4; and a light chain variable region having a light chain CDR1 described in SEQ ID NO: 6; a light chain CDR2 described in SEQ ID NO: 7; and a light chain CDR3 described in SEQ ID NO: 8; ii) a transmembrane domain; and iii) an intracellular signaling domain, which leads to T cell activation when an antigen binds to the antibody.

In the present invention, the CAR protein may be specified as being comprised of the monoclonal antibody of the present invention, a known transmembrane domain, and an intracellular signaling domain. Specifically, the CAR protein may have any nucleotide sequence encoding the amino acid sequence of SEQ ID NO: 53, and preferably, have a nucleotide sequence indicated by SEQ ID NO: 54.

The present invention provides a CAR-modified T cell capable of rapidly producing CD8+ T cells in a large scale, which can be effectively used in the immunological treatment of cancer. Specifically, in the present invention, a CAR protein, which includes an extracellular domain including the anti-MVR antibody that specifically recognizes B cell lymphoma cells, a transmembrane domain, and an intracellular domain which leads to T cell proliferation signaling when an antigen binds to the above antibody, was developed, and it was confirmed that T cell including the CAR protein is effective in treating B cell lymphoma.

The term "chimeric antigen receptor (CAR)" used herein refers to a receptor not present in nature and is capable of providing an immune effector cell with a specificity to a particular antigen. Normally, the CAR refers to a receptor used for delivering the specificity of the monoclonal antibody to a T cell. Generally, CAR consists of an extracellular domain (Ectodomain), a transmembrane domain, and an intracellular domain (Ectodomain).

The extracellular domain includes an antigen recognition region, and the antigen-binding region in the present invention is a B cell lymphoma-specific antibody, including a heavy chain variable region having a heavy chain CDR1 described in SEQ ID NO: 2; a heavy chain CDR2 described in SEQ ID NO: 3; and a heavy chain CDR3 described in SEQ ID NO: 4; and a light chain variable region having a light chain CDR1 described in SEQ ID NO: 6; a light chain CDR2 described in SEQ ID NO: 7; and a light chain CDR3 described in SEQ ID NO: 8. Preferably, the antibody used in the CAR is in the form of an antibody fragment, and more preferably, in the form of Fab or scFv, but is not limited thereto.

Additionally, the transmembrane domain of the CAR is in a form connected to the extracellular domain, and may be derived from a natural or synthesized one. When it is derived from the naturally present one, it may be one derived from a membrane-bound or transmembrane protein, and may be one derived from $\alpha$, $\beta$, or $\xi$ chain of a T cell receptor, transmembrane regions of various proteins such as CD28, CD3 epsilon, CD45, CD4, CD5, CDS, CD9, CD16, CD22, CD33, CD37, CD64, CD80, CD86, CD134, CD137, CD 154, and CD8. The sequence of the transmembrane domain may be obtained from published references in the art which disclose transmembrane domain of a transmembrane protein, but is not limited thereto.

Additionally, when the transmembrane domain is a synthetic one, it may mainly include hydrophobic amino acid residues such as leucine and valine, for example, it may be present in a transmembrane domain wherein a triplet of phenylalanine, tryptophane, and valine are synthesized, but is not limited thereto. The sequence information on the transmembrane domain may be obtained from published references in the art, but is not limited thereto. In an exemplary embodiment of the present invention, CD8-hinge region was used as a transmembrane domain.

The intracellular domain in the CAR of the present invention is part of the CAR domain, and is in a form connected to the transmembrane domain. The intracellular domain of the present invention may include an intracellular signaling domain, which is characterized in that it leads to T cell activation when an antigen binds to an antigen-binding region of the Car, and preferably, T cell proliferation.

The intracellular signaling domain is not particularly limited in its type insofar as it is a signaling part that can lead to T cell activation when the antibody binds to the antigen-binding region present extracellularly, for example, immunoreceptor tyrosine-based activation motif (ITAM), wherein the ITAM includes ones derived from CD3 zeta ($\xi$), FcR gamma, FcR beta, CD3 gamma, CD3 delta, CD3 epsilon, CDS, CD22, CD79a, CD79b, CD66d or FcεRIγ, but is not limited thereto.

Additionally, the intracellular domain of the CAR of the present invention preferably includes a co-stimulatory domain along with the intracellular signaling domain, but is not limited thereto.

The co-stimulatory domain is a part playing a role in delivering a signal to T cells, in addition to the signal by the intracellular signaling domain being included in the CAR of the present invention, and refers to an intracellular part of the CAR, including the intracellular domain of a co-stimulatory molecule.

The co-stimulatory molecule, being a cell surface molecule, refers to a molecule necessary for a sufficient response of a lymphocyte to an antigen, for example, CD27, CD28, 4-1BB, OX40, CD30, CD40, PD-1, ICOS, lymphocyte function-associated antigen-1 (LFA-1), CD2, CD7, LIGHT, NKG2C, or B7-H3, but is not limited thereto. The co-stimulatory domain may be an intracellular part of a molecule selected from the group consisting of the co-stimulatory molecules and a combination thereof.

Additionally, selectively, a short oligopeptide or polypeptide linker may connect the intracellular domain of the CAR and the transmembrane domain, and the linker may not be particularly limited with respect to its length insofar as it is a linker that can induce T cell activation through the intracellular domain when an antigen binds to the antibody present in an extracellular position, for example, GGGGSGGGGSGGGGS (SEQ ID NO: 52) called (GLY$_4$SER)$_3$.

The amino acid sequences used in the present invention are described in acronyms according to the IUPAC-IUB nomenclature as shown below.

| alanine | A | arginine | R |
| --- | --- | --- | --- |
| asparagine | N | aspartic acid | D |
| cysteine | C | glutamic acid | E |
| glutamine | Q | glycine | G |
| histidine | H | isoleucine | I |
| leucine | L | lysine | K |
| methionine | M | phenylalanine | F |
| proline | P | serine | S |
| threonine | T | tryptophan | W |
| tyrosine | Y | valine | V |

In an exemplary embodiment of the present invention, V$_H$ and V$_L$ parts of the anti-MVR antibody was connected by (GLY$_4$SER)$_3$ linker to construct an MVR scFv, and then a CAR protein, wherein the CD8-hinge was used as a transmembrane domain, and 4-1BB intracellular domain and the intracellular domain of the CD3ξ chain were sequentially connected, was constructed, and named as MVR-CAR. Additionally, in an exemplary embodiment of the present invention, a polynucleotide encoding the MVR-CAR was inserted into a lentivirus vector, and constituted such that it can be introduced into a CD8 T cell using lentivirus (Experimental Example 7).

In another aspect, the present invention provides a polynucleotide encoding the chimeric antigen receptor (CAR) protein, and a vector including the polynucleotide.

The CAR is the same as explained above.

The vector refers to a material which includes the polynucleotide encoding the CAR protein and can be used to deliver the polynucleotide inside a cell. Various vectors known in the art belong to the scope of the present invention, for example, including a linear polynucleotide, a polynucleotide to which an ionic or amphiphilic compound is bound, a plasmid, a virus, etc., but are not limited thereto. The vector may include an autonomously replicating plasmid or virus. Additionally, the vector may include a non-plasmid and non-viral compound, e.g., a liposome, etc., but is not limited thereto. Additionally, the viral vector may include adenovirus vector, adeno-associated viral vector, retrovirus vector, etc., but is not limited thereto. In an exemplary embodiment of the present invention, a recombinant lentivirus vector, which is a retroviral vector, was used.

In an aspect, the present invention provides a CAR-modified T cell which includes the polynucleotide encoding the CAR protein.

The CAR protein and the polynucleotide are the same as explained above.

The term "T cell" used herein refers to a lymphocyte which is derived from thymus and is mainly involved in cell immunity. Examples of the T cell include a CD4$^+$ T cell (helper T cell, T$_H$ cell), a CD8$^+$ T cell (cytotoxic T cell, CTL), a memory T cell, a regulatory T cell (Treg cell), an apoptotic T cell, etc. The T cell of the present invention wherein the CAR is introduced therein is preferably a CD8$^+$ T cell, but is not limited thereto.

The term "CAR-modified T cell" used herein refers to a T cell which expresses CAR. The CAR-modified T cell has advantages in that i) it recognizes cancer antigens in a human leukocyte antigen (HLA)-independent manner, reduces HLA expression on cell surfaces thus capable of treating cancers which evade the actions of anticancer agents, ii) it is irrelevant to HLA types and thus can be used for treatment, and iii) it can produce a large amount of cancer-specific T cells within a short period of time, thus exhibiting an excellent anticancer effect.

In the present invention, the CAR-modified T cell is a T cell which includes the CAR with respect to the CD74 mutant present specifically in B cell lymphoma. The antibodies located in the extracellular domain of the CAR of the present invention can specifically recognize B cell lymphoma while showing almost no reactivity to normal cells or other type of cells, and thus the T cell expressing the CAR of the present invention can exhibit a selective cancer cell removing capability in B cell lymphoma.

In an exemplary embodiment of the present invention, CD8$^+$ T cells which express the MVR-CAR were constructed, and it was confirmed that the above T cells specifically acted on B cell lymphoma, which shows an anti-MVR positive, thus having an anticancer activity (FIG. 12).

In another aspect, the present invention provides a pharmaceutical composition for preventing or treating B cell lymphoma including the CAR-modified T cell.

The CAR-modified T cell, B cell lymphoma, prevention and treatment are the same as explained above.

The CAR-modified T cell may be used alone for treating B cell lymphoma, or may be used in the form of a pharmaceutical composition in combination with a diluent or other component(s). Specifically, the pharmaceutical composition may include a CAR-modified T cell population and at least one pharmaceutically or physiologically conjugated carrier, diluents, and/or an excipient. Additionally, the composition may include neutral buffer saline, phosphate buffered saline, or other different buffer solutions, and may include a carbohydrate such as glucose, mannose, sucrose, mannitol or dextran; a protein, an amino acid such as glycine; an antioxidant, a chelating agent such as EDTA or glutathione; an adjuvant and/or an additive, but is not limited thereto. Specifically, the composition including the CAR-modified T cell may have a composition suitable for intravenous administration for adoptive cell transfer, but is not limited thereto.

In another aspect, the present invention provides a method for treating B cell lymphoma including administering the CAR-modified T cell to a subject suspected of having B cell lymphoma.

The CAR-modified T cell, B cell lymphoma, and a method of treatment thereof are the same as explained above.

In particular, the method for treating B cell lymphoma of the present invention using the CAR-modified T cell may include administering the CAR-modified T cell itself or a pharmaceutical composition containing the same to a subject suspected of having B cell lymphoma or a subject diagnosed of having B cell lymphoma, wherein the treatment is preferably performed via intravenous administration, but is not limited thereto.

In another aspect, the present invention provides a method for manufacturing the CAR-modified T cell including introducing a vector, which includes the polynucleotide encoding the CAR protein, into a separated biological sample containing T cells.

The B cell lymphoma, T cells, CAR protein, and CAR-modified T cell are the same as explained above.

The term "biological sample" used herein refers to a sample such as a cell, a tissue, whole blood, blood serum, or blood plasma separated from a subject, including T cells.

Preferably, the biological sample is a sample containing T cells separated from a subject suspected of or diagnosed as having B cell lymphoma, and the CAR-modified T cell may be manufactured by introducing the vector including the polynucleotide encoding the CAR protein into a T cell separated from the subject suspected of or diagnosed as having B cell lymphoma.

In an exemplary embodiment of the present invention, CD8+ T cells expressing the MVR-CAR were manufactured using lentivirus which includes the MVR-CAR gene (Experimental Example 7).

In another aspect, the present invention provides an antibody-drug conjugate wherein the monoclonal antibody and a drug are conjugated.

The antibody is the same as explained above.

The term "antibody-drug conjugate (ADC)" used herein refers to a conjugate wherein the monoclonal antibody of the present invention and a drug are conjugated, and may also be called an immunoconjugate. The antibody-drug conjugate may be manufactured by various methods known in the art.

The term "drug" used herein refers to materials, without limitation, which, being conjugated to the antibody of the present invention, can be used for treating diseases, by increasing the efficiency itself, increasing the half-life of the antibody in the blood, or arriving at the target position and apoptosizing cancer, etc., in the target, for example, cytotoxic drugs, toxins, antibiotics, enzyme such as nucleases, radionuclides, etc., but is not limited thereto.

The cytotoxic drug refers to a drug which may be used for treating diseases, and preferably, a drug having an anticancer activity, and it includes inhibitor of microtubulin structure formation, meiosis inhibitor, topoisomerase inhibitor and DNA intercalator. Examples of the cytotoxic drug include maytansinoid, auristatin, dolastatin, trichothecene, CC-1065 drug (NSC 298223), calicheamicin, enediynes, taxane, anthracycline, methotrexate, adriamycin, vindesine, vinca alkaloid, doxorubicin, melphalan, mitomycin C, chlorambucil, daunorubicin, daunomycin, etoposide, teniposide, carminomycin, aminopterin, dactinomycin, bleomycin, esperamicin, 5-fluorouracil, melphalan, nitrogen mustard (mechlorethamine HCL), cis-platinum and its homologues, cisplatin, CPT-11, doxorubicin, and docetaxel.

The term "toxin" used herein refers to a drug having a toxin produced by a bio-organism, and may include plant toxins, animal toxins, exotoxins, bacterial toxins, etc., although not particularly limited thereto.

Additionally, examples of the radionuclides include $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, $^{186}Re$, etc., but are not limited thereto.

The monoclonal antibody of the present invention specifically recognizes only B cell lymphoma, and thus it can be used in treating B cell lymphoma in various forms including an antibody-/anticancer-therapeutic agent, an antibody-drug conjugate, and a CAR T cell treatment.

BRIEF DESCRIPTION OF THE DRAWINGS

FIG. 6 shows the analysis result of the sequence of the anti-MVR antibody of the present invention.

DETAILED DESCRIPTION OF PREFERRED EMBODIMENTS

Figure 1:
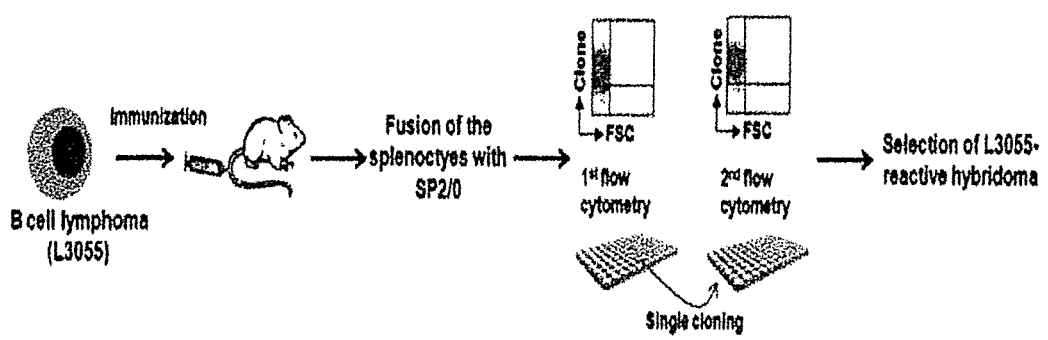
FIG. 1 is a schematic diagram illustrating a process of manufacturing a hybridoma which recognizes cell surface proteins of B cell lymphoma.

Preferred embodiments of the present invention will be described below in more detail with reference to the accompanying drawings. The present invention may, however, be embodied in different forms and should not be constructed as limited to the embodiments set forth herein. Rather, these embodiments are provided so that this disclosure will be thorough and complete, and will fully convey the scope of the present invention to those skilled in the art.

EXAMPLE 1

Antibodies and Reagents

The anti-CD74 monoclonal antibody MB741, anti-HLA-DR-FITC, anti-CD19-FITC, anti-CD3 monoclonal antibody, and anti-mouse IgG-FITC & PE were purchased from BD Phamingen, the anti-CD74 monoclonal antibody By2 was purchased from Santa cruz, and the alexa Fluor 546 anti-mouse IgG was purchased from Invitrogen.

Additionally, recombinant human IL-2 was purchased from Peprotech. RAG2$^{-/-}$ c$^{-/-}$ mice were provided by Central Institute for Experimental Animals (CIEA, Japan). Hela-CIITA (class II transactivator) cell line was provided by Dr. Philippe Pierre (Centre d'Immunologie de Marseille-Luminy, Marseille, France).

EXAMPLE 2

Cell Line

L3055 cells were cultured in a medium prepared by adding 10% FBS, 3 mM glutamine, 100 U/mL penicillin G, and 100 µg/mL streptomycin to Iscoves modified Dulbeccos medium (IMDM, Irvine Science, Santa Ana, Calif.). THP-1, 293, PC3, Jurkat, CCRF-CEM, A431, 1A2, JVM2, and BC-1 cell lines were purchased from ATCC cell line bank (Manassas, Va.), and SNU638, SNU20, and SNU538 cell lines were provided by the Korean Cell Line Bank (KCLB, Seoul, Korea). EBV-transformed lymphoblastoid cells (LCL) were prepared by infecting peripheral blood mononuclear cells (PBMCs) with a EBV B95-8 cell line, and then culturing in an RPMI1640 medium (WellGene, Korea), which was prepared by adding 10% FBS and antibiotics in a state provided with 1 µg/mL CsA.

EXAMPLE 3

Construction of B cell Lymphoma-Specific Monoclonal Antibody

A balb/c mouse was intraperitoneally injected with 2×10$^7$ of L3055 cell line a total of two times every two weeks. Three weeks after the second injection, 1×10$^7$ of the same cells were intravenously injected. On the 4$^{th}$ day from the final immune injection, the spleen cells of the mice were separated and fused using SP2/0 myeloma cells and PEG. The fused cells were aliquoted into a 96-well plate at a concentration of 5×10$^5$ cells/well, added with a HAT selective medium containing hypoxanthine (H) and aminopterin, and cultured thereafter.

EXAMPLE 4

Separation of B cell Lymphoma-Specific Hybridomas

In order to select B cell lymphoma-specific hybridoma clones, culture supernatants containing 1 to 10 hybridoma colonies were collected from each well, and used for staining the cell surface of L3055 cells. Then, the hybridomas in the positive well, which showed reactivity in flow cytometry analysis, were again aliquoted into a 96-well plate at a concentration of 2 cells/well, and performed a single cell cloning. On the 14$^{th}$ day of the culture, the culture supernatant containing one hybridoma colony was collected, and used it as a primary antibody for staingin the cell surface of L3055 cells to perform flow cytometry analysis.

EXAMPLE 5

Identification of Proteins Recognized by Anti-MVR Monoclonal Antibody

In order to separate proteins recognized by the anti-MVR monoclonal antibody, 10 mg of anti-MVR antibodies were passed through a column filled with 1 mL of protein A/G resin (Santa Cruz) to be conjugated, cross-linked using disuccinimidyl suberate, washed with PBS several times, and a column filled with anti-MVR mAb-cross-linked resin was prepared. LCL or 1A2 cells (2×10$^8$ cells) were suspended in Tris-buffered saline (TBS, 50 mM pH 7.5 Tris, and 150 mM NaCl) and homogenized the cells using a glass homogenizer. Cell debris was removed by centrifugation, and only the supernatant was recovered to prepare a cell lysate, which was repeatedly passed through an affinity column already prepared. Then, the resultant was washed 3 times with TBS, and then the conjugated proteins were separated using 100 mM glycine solution (pH 3.0). The proteins were concentrated via trichloroacetic acid precipitation method, and the separated proteins were separated on a 12% SDS-PAGE gel. The proteins separated on the gel were stained with silver SNAP kit (Pierce), and the protein bands identified under naked eye were cut out to perform QTOF (ESI-MS/MS).

EXAMPLE 6

Western Blotting

Each sample was diluted with 5× SDS sample buffer solution, electrophoresed on an SDS-PAGE gel, and transferred to a nitrocellulose membrane (Millipore, Bedford, Mass.). CD74 protein was detected using the anti-CD74 monoclonal antibody (By-2 clone) and secondary antibodies-HRP, and allowed to develop color using ECL kit (Amersham Pharmacia Biotech, Little Chalfont, UK).

EXAMPLE 7

Short Interference RNA (siRNA) Transfection

According to the report by Liu YH et al (*J Immunol* 2008; 181: 6584-94), siRNA of CD74 (5'-GCAA-CAUGACAGAGGACCATGTGAC-3', SEQ ID NO: 17) was synthesized.
After adding 0.5 mL of LCL cells at a concentration of $4 \times 10^6$ cells/mL, and then 100 pM and 500 pM CD74 siRNA to a 0.4 cm cuvette were, an electroporation was performed under the conditions of 250 volt and 950 μF using GenePulser Xcell™ (Bio-Rad). Then, after culturing in a 6-well plate for 36 hours, the resultant was subjected to flow cytometry analysis and western blotting.

EXAMPLE 8

Expression of Recombinant CD74 Isoforms

In order to prepare GFP-fused CD74 isoforms, each of PCR products of CD74 isoforms of p33, p41, and p43 was inserted into the Xho I/EcoR I site of pAcGFP1-C3 vector (Clontech, Calif.).
Among the CD74 isoforms, p35 and p43 used 5'-CTCGAGATGCACAGGAGAAGCAGGA-3' (SEQ ID NO: 18) as a forward primer, whereas p41 used 5'-CTCGAGATGGATGACCAGCGCGACC-3'(SEQ ID NO: 19) as the forward primer. As a reverse primer, all three used 5'-GAATTCTCACATGGGGACTGGGCC-3' (SEQ ID NO: 20) for amplification.
The thus prepared pAcGFP-p33, -p41, and -p43 were introduced into HeLa-CIITA cells via Lipofectamin™ 2000 (Invitrogen). Then, each cell was cultured for 36 hours, and their GFP expression was observed under fluorescent microscope.

EXAMPLE 9

Conjugation Between a Malignant B Cell of a Patient and an Anti-MVR Monoclonal Antibody All the blood and tissue samples used in the present invention were provided after IRP approval, and the experiments were performed in a research laboratory of National Cancer Center Korea.
Specifically, a 15 mL conical tube was filled with 5 mL of Ficoll, and then a blood sample collected from a chronic lymphocytic leukemia (CLL) or acute lymphocytic leukemia (ALL) patient was placed on top of the Ficoll solution, and centrifuged under the condition of 840×g/20. Then, the monocytes located between the Ficoll solution and blood plasma were collected and washed. Additionally, for staining of cell surfaces, the separated cells were added with human AB serum, and treated with PE-conjugated anti-CD19 monoclonal antibodies (mAb) along, PE-anti CD19+FITC-conjugated anti-MVR monoclonal antibodies, PE-anti CD19+anti-CD74 MB741 monoclonal antibodies, respectively. For intracellular staining, the separated cells were added with human AB serum, and stained the cell surface with PE-conjugated anti-CD19 monoclonal antibodies, and then fixed/permeabilized the CD19-stained cells using a Cytofix/Cytoperm solution. Then, the resultant was intracellularly stained with anti-MVR monoclonal antibodies or the anti-CD74 monoclonal antibodies MB741, respectively.
In contrast, a frozen tissue section of a diffused large B-cell lymphoma (DLBCL) patient obtained from the Catholic Research Tissue Specimen Bank (Seoul, Korea) was fixed using a Cytofix/Cytoperm solution, and stained with the anti-MVR monoclonal antibodies for 2 hours. The stained tissues were washed and subjected to secondary staining with the anti-mouse IgG-HRP. Then, the resultant was allowed to develop color by treating with 3'-diaminobenzidine, and then counterstained with hematoxylin. All the samples were fixed with the permanent mounting solution, covered with a coverslip and photographed under fluorescent microscope.

EXPERIMENTAL EXAMPLE 1

Selection of B Cell Lymphoma-Specific Anti-MVR Hybridoma

A balb/c mouse was repeatedly subjected to an immune injection with live B cell lymphoma L3055 cells of human origin at 2 week intervals, and on the $4^{th}$ day after the third immune injection, the spleen cells of the mouse were separated and fused with SP2/0 myeloma cells. The fused cells were aliquoted into a 96-well plate at a concentration of $1 \times 10^6$ cells/well, and cultured in a state where 1× HAT was contained therein. On the $14^{th}$ day of the culture, the L3055 cells were subjected to flow cytometry analysis using the supernatant in each well as the primary antibodies. The wells which showed high reactivity to L3055 cells were selected, and the cells in the selected wells as containing about 1 to 10 hybridoma colonies were subjected to a single cloning in the manner again aliquoted into the 96-well culture plate. After 14 days, the wells having a single colony were selected, and the reactivity to L3055 cells was analyzed via flow cytometry using the culture supernatant in each well as the primary antibodies, and thirty some hybridomas producing the monoclonal antibodies capable of recognizing the surface proteins of the L3055 cells were selected (FIG. 1).
Additionally, in order to select the hybridomas which specifically react only to B cell lymphoma, among the selected hybridomas capable of recognizing the L3055 cell surface proteins through the process illustrated in FIG. 1, the reactivity of the primarily selected hybridomas regarding various cancer cells, instead of B cell lymphomas such as THP-1, 293, SNU638, PC3, Jurkat, CCRF-CEM, and A431, were examined.
As a result, only four kinds of hybridomas (anti-MVR, IRC97, IRC120, and IRC278 hybridomas) among the thirty some hybridomas were shown to have no reactivity to the cancer cells (FIG. 2A).

As such, the secondarily selected four kinds of hybridomas were subjected to a third examination whether they also had high reactivity to six different kinds of B cell lymphoma cell lines.

Figure 2:
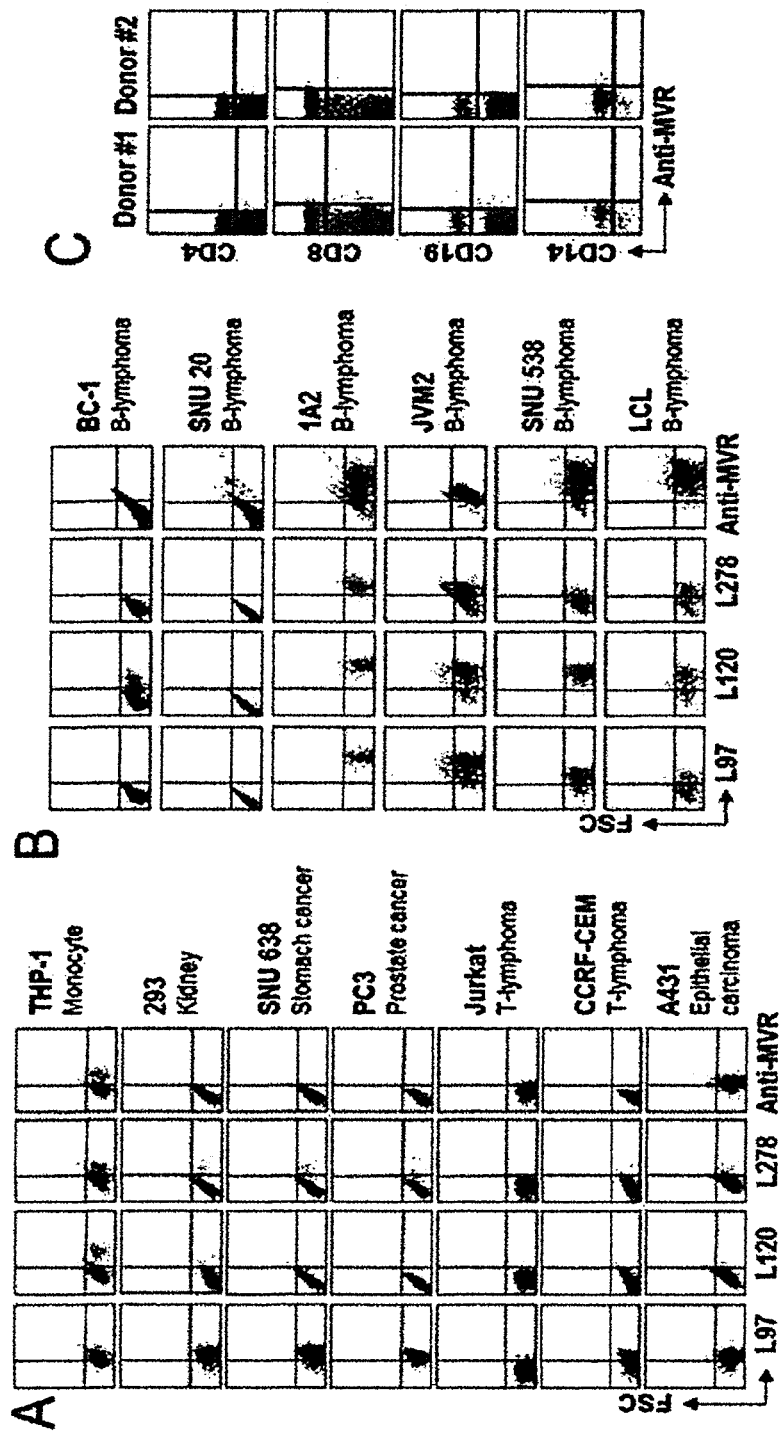
FIG. 2 is a chart illustrating a process of selecting hybridomas which react specifically with B cell lymphoma; wherein (A) shows the result of flow cytometry analysis, after primary staining of various cancer cells with the culture supernatants of anti-MVR, IRC97, IRC120, and IRC278 hybridomas for 30 minutes, followed by staining of their cell surfaces with anti-mouse IgG-FITC antibodies; (B) shows the result of flow cytometry analysis, after primary staining of 6 kinds of B cell lymphoma cells with the culture supernatants of anti-MVR, IRC97, IRC120, and IRC278 hybridoma for 30 minutes, followed by staining of the B cell lymphoma cells with anti-mouse IgG-FITC antibodies; and (C) shows the result of flow cytometry analysis, after staining the peripheral blood mononuclear cells, (PBMC) separated from the blood of two healthy volunteers, with anti-MVR-FITC antibodies, and anti-CD4, -CD8, -CD19, and -CD14-PE, respectively.

As a result, the anti-MVR hybridoma, among the four different kinds of hybridomas, showed the highest reactivity to 1A2, JVM2, SNU538, and LCL, among the six different kinds of B cell lymphomas, and the lowest reactivity to BC1 and SNU20 cells (FIG. 2B). In particular, the flow cytometry analysis revealed that although the anti-MVR hybridoma showed a strong reactivity to various kinds of B cell lymphoma cells, it did not react with CD4+ T cells, CD8+ T cells, and CD14+ monocytes including normal CD19+ B cells, and also did not react with any lymphocytes (FIG. 2C).

The above results imply that the anti-MVR monoclonal antibody can recognize membrane proteins present only in B cell lymphomas.

EXPERIMENTAL EXAMPLE 2

Confirmation of Binding-Antigen of Anti-MVR Monoclonal Antibody

In order to identify the membrane proteins recognized by the anti-MVR monoclonal antibody based on the result of Experimental Example 1, an anti-MVR mAb-crosslinking affinity purification column was prepared. Then, cell lysates were prepared from LCL and 1A2, and repeatedly passed through the prepared affinity purification column. Then, the proteins separated from the column was separated on a 12% SDS-PAGE gel, and subjected to silver staining.

Figure 3:
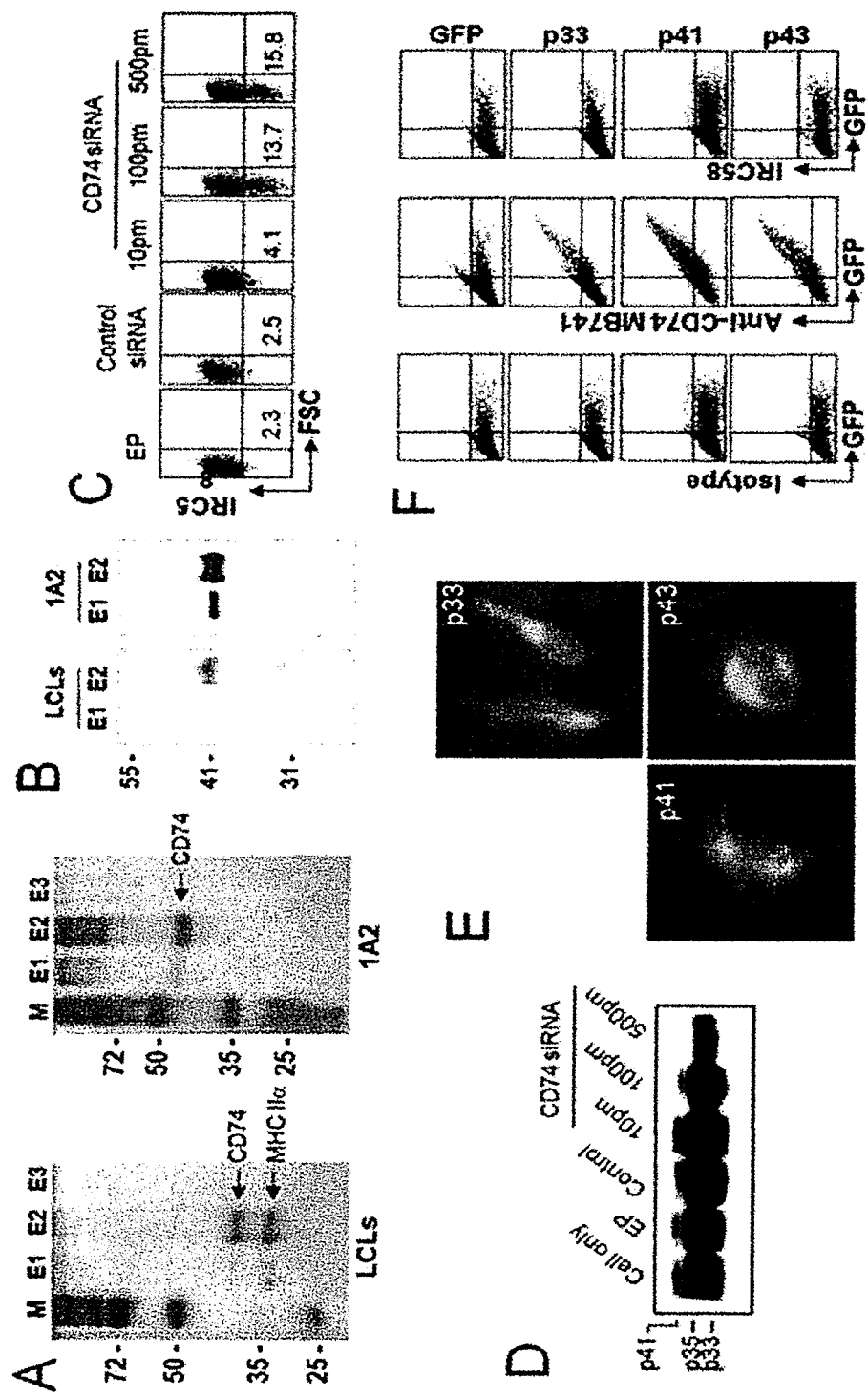
FIG. 3 shows the process of identifying membrane proteins which bind to anti-MVR antibodies. With respect to (A-B), in order to identify the cell surface proteins recognized by anti-MVR monoclonal antibodies, anti-MVR antibodies were crosslinked to protein A/G-agarose resin, filled into an empty column, and proteins antigenic to the anti-MVR antibodies were allowed to bind to the anti-MVR antibodies by passing a cell lysate prepared using LCL or 1A2 B cell lymphoma cells through the column. After washing the column 3 times, the proteins bound to the anti-MVR antibodies were extracted using 100 M glycine (pH 3.0) solution. The extracted proteins were separated on a 12% SDS-PAGE gel and the separated proteins were stained with silver for visual recognition. The protein bands appeared by the silver staining were cut out and subjected to Q-TOF analysis for their identification. With respect to (B), the proteins, which were shown to bind to the anti-MVR antibodies in the previous process, were separated on a 12% SDS-PAGE gel, transferred to a nitrocellulose membrane, and subjected to western blotting analysis using anti-CD74 monoclonal antibodies. With respect to(C), LCL B cell lymphoma cells, which show high reactivity with the anti-MVR monoclonal antibodies were transfected with CD74 siRNA at varied concentrations, and their reactivities to the anti-MVR monoclonal antibodies were analyzed via flow cytometry. With respect to (D), the LCLs cells transfected with the CD74 siRNA were analyzed via western blotting using the anti-CD74 monoclonal antibodies. With respect to (E-F), HeLa-CIITA cells were transfected with a plasmid, which expresses GFP-CD74 p35, GFP-CD74 p41, and GFP-CD74 p43, and cultured for 36 hours. The cells which express GPF were confirmed under fluorescent microscope (E), and upon confirmation of GFP expression, the cells were analyzed via flow cytometry after the primary staining each of the cells with anti-CD74 mAb MB741 or anti-MVR antibodies, followed by staining with anti-mouse IgG-PE (F).

As a result, two proteins were separated from LCL cells, and one protein was separated from 1A2 cells (FIG. 3A). When the separated proteins were cut out of the gel and analyzed via Q-TOF, the protein with about 30 kDa was identified to be a HLA class histocompatibility antigen, and the protein of about 40 kDa was identified to be a CD74 antigen (invariant chain) (FIG. 3A).

Human CD74 protein is a type II membrane protein, and there are p33, p35, p41, and p43 isoforms (Henne C et al., Immunology 1995; 84: 177-82). Accordingly, the protein with about 30 kDa separated by the anti-MVR antibodies was speculated to be p41 or p43 CD74. For its confirmation, the proteins which were passed through affinity purification by the anti-MVR monoclonal antibodies were subjected to western blotting using the anti-human CD74 antibodies.

As a result, the proteins separated by the anti-MVR antibodies was shown to be recognized by the anti-human CD74 antibodies, and their size was determined to be 41 KDa (FIG. 3B).

Additionally, in order to further confirm whether the proteins separated recognized by the anti-human CD74 antibodies are CD74, the LCL cell line, which showed high reactivity to the anti-MVR antibodies, was transfected with CD74 siRNA.

As a result, as the amount of the CD74 siRNA increased the number of cells not stained by the anti-MVR antibodies increased (FIG. 3C), and also the western blotting analysis using the anti-CD74 antibodies revealed that as the amount of the CD74 siRNA increased the expression of CD74 isoforms decreased (FIG. 3D).

In order to directly confirm whether the anti-MVR monoclonal antibody can recognize p41 CD74, a Hela-CII TA cell line was overexpressed with p33, p41, and p43 CD74 isoforms.

As a result, it was confirmed that each of the CD74 isoforms fused with the GFP fluorescent protein was a bit different from each other (FIG. 3E). Additionally, although the anti-CD74 antibodies were shown to recognize all the overexpressed CD74 isoforms, the anti-MVR monoclonal antibody of the present invention was shown not to recognize the overexpressed CD74 isoforms (FIG. 3F).

From the foregoing results, the anti-MVR monoclonal antibody of the present invention was speculated to recognize a CD74 variant (CD74v), which has not been known.

EXPERIMENTAL EXAMPLE 3

Confirmation of Reactivity of Anti-MVR Monoclonal Antibody to Cancer Cells of a Clinical B Cell Lymphoma/Leukemia Patient Although the above Experimental Examples confirmed that the anti-MVR monoclonal antibody of the present invention had high reactivity to various kinds of B cell lymphoma cell lines, it was not certain whether it also had high reactivity to B cell lymphoma/leukemia cells of a real clinical cancer patient. Accordingly, the specificity of the anti-MVR monoclonal antibody to the clinical B cell lymphoma/leukemia cells was examined.

For B cell leukemia, one bone marrow and two blood samples were obtained, and for B cell lymphoma, frozen tissue sections of a diffused large B-cell lymphoma (DLBCL) of four different patients. Additionally, lymphocytes were separated from bone marrow and blood of all B cell leukemia patients; and the blood of CLL patients, and their cell surfaces were stained with the anti-CD19-PE antibodies, and then they were subjected to intracellular or cell surface staining with anti-CD74-FITC(MB741) or anti-MVR-FITC, respectively. In particular, the protein level expressed on the cell surfaces was confirmed via cell surface staining, whereas the entire expression level of CD74v and CD74 of the B cell leukemia cells was confirmed via intracellular staining.

Figure 4:
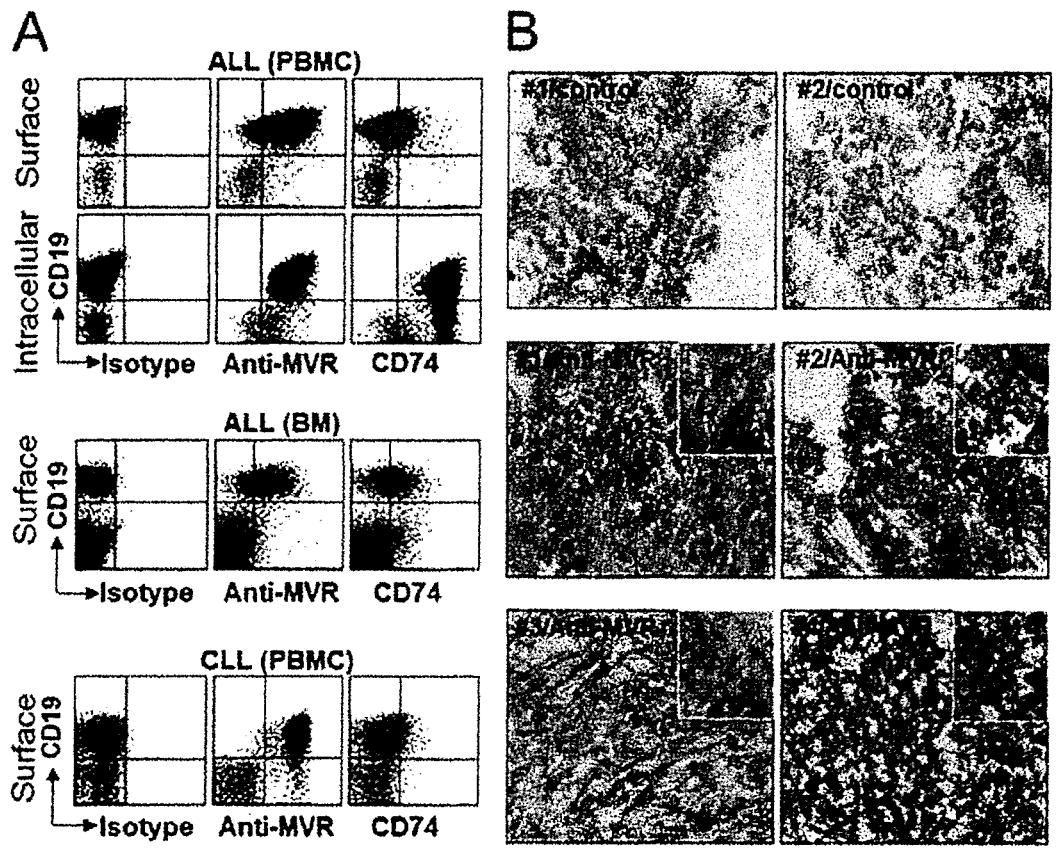
FIG. 4 shows the images of reactivity of the anti-MVR monoclonal antibodies to the B cell lymphoma/leukemia cells of a clinical cancer patient. With respect to (A), immune cells were subjected to flow cytometry analysis after separating the immune cells from the blood or bone marrow of ALL or CLL patients, and staining their cell surfaces with anti-CD19-PE antibodies, followed by the intracellular or cell surface staining with anti-MVR-FITC antibodies. With respect to (B), it shows the results of immunochemical staining of the cancer tissues of four different DLBCL cancer patients using the anti-MVR monoclonal antibodies.

Accordingly, the results of cell surface staining and intracellular staining revealed that CD74v, which is recognized by the anti-MVR antibodies, showed a high expression rate similar to the cell surface and intracellular levels, but CD74 was partially present on cell surface although its expression rate was high (FIG. 4A). Additionally, the result of flow cytometry analysis of cell surface expression of CD74v and CD74 of bone marrow lymphocytes of ALL patients revealed that CD74v and CD74 were expressed at a similar level in the B cell leukemia cells of bone marrow (FIG. 4A). The result of cell surface expression of CD74v and CD74 with respect to the blood lymphocytes of CLL patients revealed that CD74v, which is recognized by the anti-MVR monoclonal antibody, was expressed on cell surface at a high level but the expression level of CD74 was low (FIG. 4A).

Since the anti-MVR monoclonal antibody cannot recognize modified proteins it cannot stain paraffin tissues. Accordingly, frozen tissues obtained from four different DLBCL patients were cut out to have a thickness of 5 μm, stained with the anti-MVR monoclonal antibodies, secondarily stained with the anti-mouse IgG-HRP to develop color, thereby confirming the presence of conjugation with the anti-MVR antibodies.

As a result, it was confirmed that CD74v was expressed in the cancer cells of most DLBCL patients subjected to histochemical staining (FIG. 4B).

The above results suggest that the anti-MVR monoclonal antibody of the present invention can recognize the clinical B cell lymphoma/leukemia cancer cells.

EXPERIMENTAL EXAMPLE 4

Identification of Nucleotide and Amino Acid Sequences of the Heavy Chain and the Light Chain of Anti-MVR Monoclonal Antibody After isolating total RNA from 1×10⁶ cells of the anti-MVR hybridoma using TRIZOL, a single stranded cDNA was constructed using superscript III kit (Invitrogen). For amplification of the variable regions of the light chain and the heavy chain of the anti-MVR antibody, PCR was performed using the primer set described in Tables 1 and 2 below.

TABLE 1

Primer sequences to amplify
the variable region of light chain
(Y:CT; R:AG; W:AT; M:AC; S:GC; H:ACT)

| | | SEQ ID NO |
|---|---|---|
| Forward primers for variable region of light chain (5'->3') | | |
| MVK1 | GCTACCGTAGCACAGGCAGCCGAYATCCAGATGACACARWC | 21 |
| MVK2 | GCTACCGTAGCACAGGCAGCCGAAAWTGTGCTCACCCAGTC | 22 |
| MVK3 | GCTACCGTAGCACAGGCAGCCGACATTGTGCTRACMCAGTC | 23 |
| MVK4 | GCTACCGTAGCACAGGCAGCCGACATTGTGATGTCACAGTC | 24 |
| MVK5 | GCTACCGTAGCACAGGCAGCCGATATTGTGCTAACTCAGTC | 25 |
| MVK6 | GCTACCGTAGCACAGGCAGCCGACATCYGGATGACTCAGTC | 26 |
| MVK7 | GCTACCGTAGCACAGGCAGCCAACATTGTRMTGACCCAATC | 27 |
| MVK8 | GCTACCGTAGCACAGGCAGCCGACATYCAGATGACHCAGTC | 28 |
| MVK9 | GCTACCGTAGCACAGGCAGCCGAAACAACTGTGACCCAGTC | 29 |
| MVK10 | GCTACCGTAGCACAGGCAGCCGACATTGTGCTSACCCAATC | 30 |
| Reverse primer (5'->3') | | |
| MCK | GTTGTTCAAGAAGCACACGACTGA | 31 |

TABLE 2

Primer sequences to amplify the
variable region of heavy chain (Y:CT; R:AG;
W:AT; M:AC; S:GC; K:TG; H:ACT; B:AGT; V:ACG)

| | | SEQ ID NO |
|---|---|---|
| Forward primers for variable region of heavy chain (5'->3') | | |
| MVH1 | ATGGCCGAGGTRMAGCTTCAGGAGTC | 32 |
| MVH2 | ATGGCCGAGGTBCAGCTBCAGCAGTC | 33 |
| MVH3 | ATGGCCGAGGTGCAGCTGAAGSASTC | 34 |
| MVH4 | ATGGCCGAGGTCCARCTGCAACARTC | 35 |
| MVH5 | ATGGCCGAGGTYCAGCTBCAGCARTC | 36 |
| MVH6 | ATGGCCGAGGTYCARCTGCAGCAGTC | 37 |
| MVH7 | ATGGCCGAGGTCCACGTGAAGCAGTC | 38 |
| MVH8 | ATGGCCGAGGTGAASSTGGTGGAATC | 39 |
| MVH9 | ATGGCCGAGGTGAWGYTGGTGGAGTC | 40 |
| MVH10 | ATGGCCGAGGTGCAGSKGGTGGAGTC | 41 |
| MVH11 | ATGGCCGAGGTGCAMCTGGTGGAGTC | 42 |
| MVH12 | ATGGCCGAGGTGAAGCTGATGGARTC | 43 |
| MVH13 | ATGGCCGAGGTGCARCTTGTTGAGTC | 44 |
| MVH14 | ATGGCCGAGGTRAAGCTTCTCGAGTC | 45 |
| MVH15 | ATGGCCGAGGTGAARSTTGAGGAGTC | 46 |
| MVH16 | ATGGCCGAGGTTACTCTRAAAGWGTSTG | 47 |
| MVH17 | ATGGCCGAGGTCCAACTVCAGCARCC | 48 |
| MVH18 | ATGGCCGAGGTGAACTTGGAAGTGTC | 49 |
| MVH19 | ATGGCCGAGGTGAAGGTCATCGAGTC | 50 |
| Reverse primer (5'->3') | | |
| MVC | AGGACAGCCGGGAAGGTGTGCAC | 51 |

Figure 5:
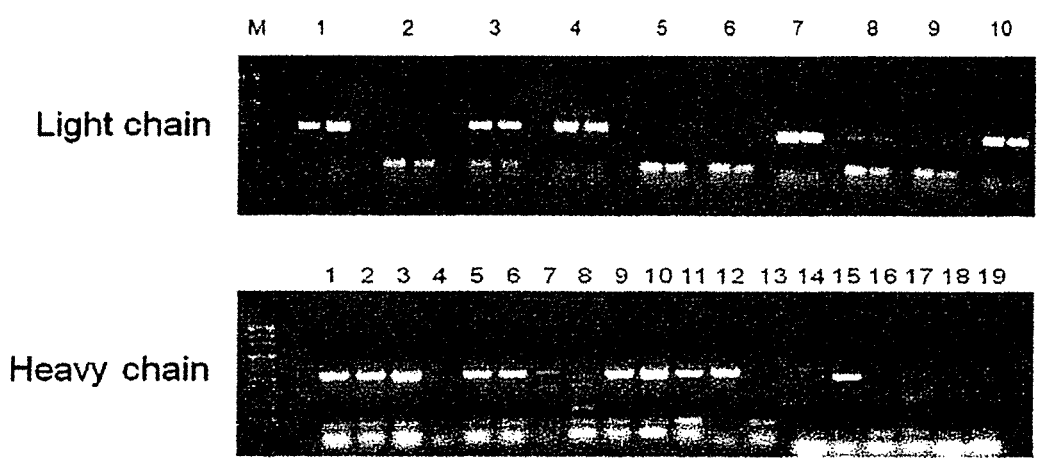
FIG. 5 shows the results of PCR amplification of the light chain and the heavy chain of the anti-MVR antibodies. After separating the total RNA from the anti-MVR hybridoma, single stranded cDNA was synthesized using Superscript II (Invitrogen). A PCR was performed using the cDNA as a template and the forward and reverse primer set. The PCR amplified DNA was separated on a 1.5% agarose gel.

As a result of separation of PCR products amplified using each primer set from an agarose gel, it was confirmed that, in the case of the variable region of the light chain, the gene was amplified by MVK1, 3, 4, 7 and 10 primers, whereas, in the case of the variable region of the heavy chain, the gene was amplified by MVH 1, 2, 3, 5, 6, 9, 10, 11, 12 and 15 primers (FIG. 5).

The sequences were identified and the results are shown in FIG. 6. Additionally, the amino acid sequence of the heavy chain variable region of the anti-MVR antibody was indicated in SEQ ID NO: 1, that of the heavy chain CDR1 was indicated in SEQ ID NO: 2, that of the heavy chain CDR2 was indicated in SEQ ID NO: 3, that of the heavy chain CDR3 was indicated in SEQ ID NO: 4, that of the light chain variable region was indicated in SEQ ID NO: 5, that of the light chain CDR1 was indicated in SEQ ID NO: 6, that of the light chain CDR2 was indicated in SEQ ID NO: 7, and that of the light chain CDR3 was indicated in SEQ ID NO: 8 (FIG. 6).

Figure 7:
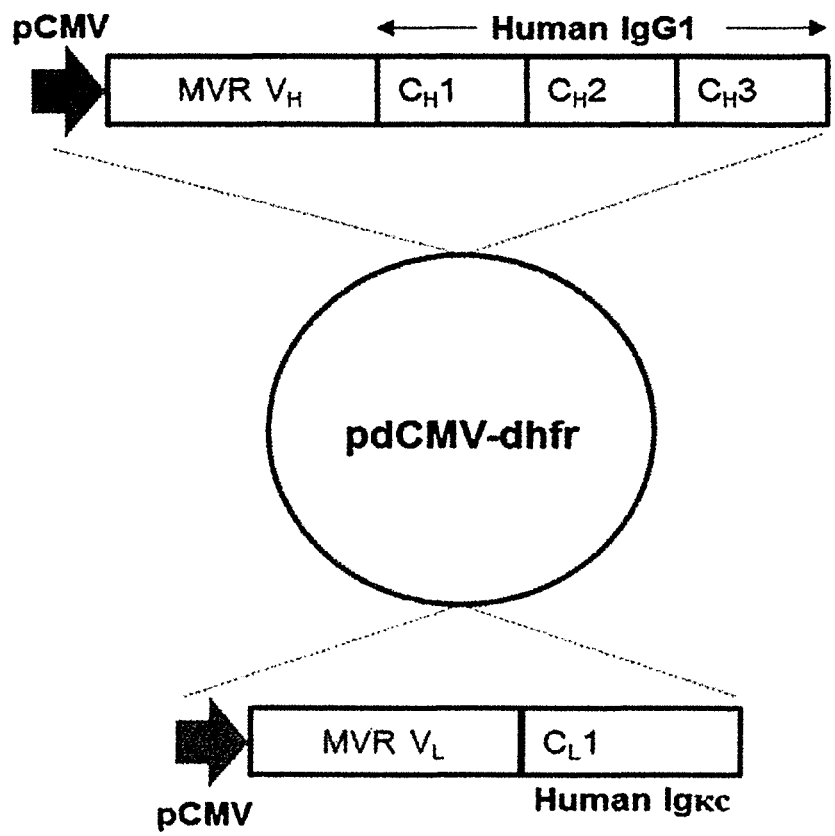
FIG. 7 shows a schematic diagram illustrating the constitution of the DNA construct for expressing a chimeric anti-MVR antibody.

Additionally, in order to finally confirm whether the cloned anti-MVR heavy chain variable region (anti-MVR VH) and the light chain variable region (anti-MVR VL) are anti-MVR antibodies, the anti-MVR VH was conjugate to CH1, CH2, and CH3, which are constant regions of human IgG1 isotypes, whereas the anti-MVR VL was conjugated to CL1 of human Igκc, and cloned into pdCMV-dhfr vector, as illustrated in the diagram of FIG. 7. For the expression of the entire form of the thus prepared chimeric anti-MVR antibody (chiMVR), a construct was prepared.

The thus prepared DNA construct was transfected into a HEK 293 cell line, cultured for two days, and LCL cells were subjected to cell surface staining using the culture supernatant as the primary antibodies. Epstein-Barr virus-transformed lymphoblastoid cell lines (EBV-LCL) is a representative cancer cell line which overexpresses CD74v protein recognized by the anti-MVR antibody. Accordingly, the EBV-LCL cells were stained with the chiMVR expressed in the HEK293 cells and the anti-MVR antibodies, and the staining pattern was analyzed via flow cytometry. Since the parental anti-MVR antibody is a mouse IgG form, it was stained using the anti-mouse IgG-FITC, whereas, chiMVR antibody, which is a human IgG form, was stained using the anti-human IgG-FITC.

Figure 8:
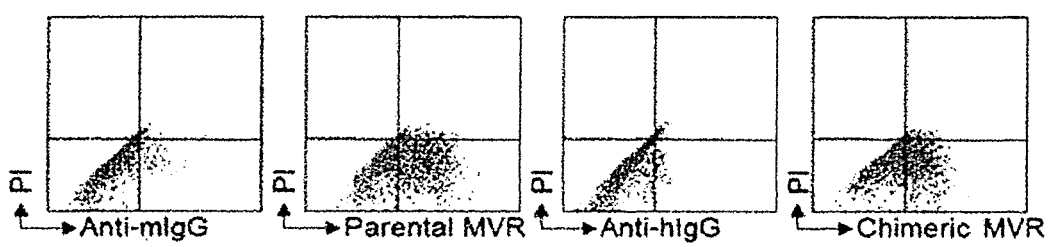
FIG. 8 shows the result of flow cytometry analysis using the chimeric anti-MVR antibody. Specifically, a pdCMV-dhfr-chiMVR gene was introduced to the 293 cell, and cultured at 37° C. for two days. The LCL cells were analyzed via flow cytometry after staining them with a culture supernatant including the ChiMVR antibody or the anti-MVR antibody, followed by a secondary staining with an anti-mouse IgG or anti-human IgG-FITC.

As a result, the anti-MVR antibodies and the chiMVR antibodies were conjugated to the EBV-LCL in the same pattern, as shown in FIG. 8. Accordingly, the cloned VH and VL were determined to be the VH and VL of the anti-MVR antibodies.

EXPERIMENTAL EXAMPLE 5

Confirmation of In Vitro Anticancer Activity of ChiMVR Monoclonal Antibody against B Cell Lymphoma Since the ChiMVR monoclonal antibody has a human IgG1 Fc region, antibodies-dependent cytotoxicity (ADCC) by human natural killer (NK) cells can be measured. Accordingly, a blood sample was obtained from a single donor and then LCL, a B cell lymphoma transformed into EVB, was constructed, and simultaneously, the human NK cells separated from the same donor's blood was cultured and prepared effector cells and target cells to perform in vitro ADCC. Then, LCL stained with ChiMVR antibodies and LCL not stained with ChiMVR antibodies were prepared, and the LCL cells were labeled with $^{51}Cr$ for one hour. The NK cells as the effector cells, and the LCL as the target cells were mixed at a ratio of 10:1, 1:1, 1:10, and 1:100, cultured for 4 hours, and the released amount of $^{51}Cr$ was measured.

Figure 9:
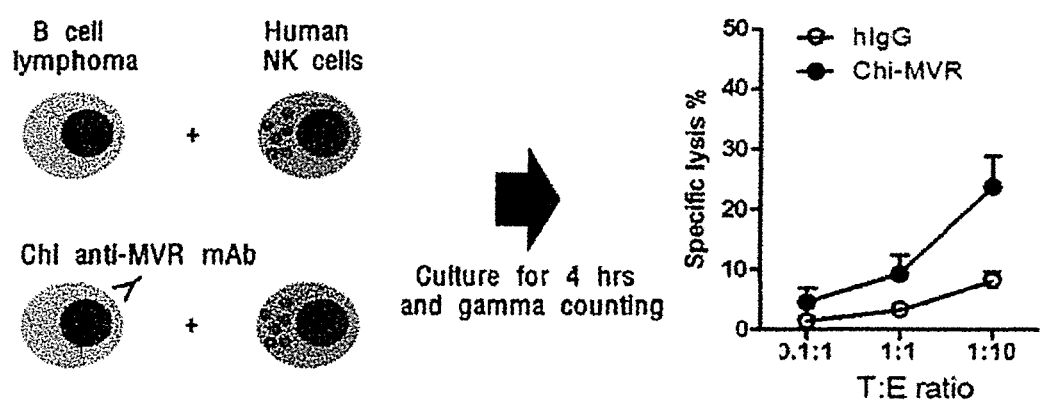
FIG. 9 shows the results of in vitro ADCC using the ChiMVR antibody. Specifically, the LCL cells were stained with chiMVR or human IgG for 30 minutes and then labeled with $^{51}$Cr for 1 hour. Human NK cells were cultured for 14 days in PBMC separated from the blood after treating with 10 ng/mL anti-CD3 mAb and 500 IU/mL human recombinant IL-2. After mixing the prepared NK cells and LCL cells in a ratio indicated in the picture and culturing for 4 hours, the ADCC was measured based on the amount of $^{51}$Cr released into a medium.

As a result, the EBV-LCL cells were shown to be highly induced of their cell lysis by NK cells compared to the cells labeled with the human IgG, as shown in FIG. 9.

The above results suggest that when the chiMVR antibodies are attached to the LCL cells, they increase the cell lysis of NK cells thereby providing an anticancer effect.

EXPERIMENTAL EXAMPLE 6

In Vivo Anticancer Activity of ChiMVR Monoclonal Antibody Against B Cell Lymphoma 1A2 and LCL B cell lymphoma cells, which showed high reactivity to the anti-MVR antibodies, were aliquoted into a 96-well culture plate, added with the anti-MVR antibodies or mouse IgG as a control group, and cultured the cells for five days. Specifically, they were aliquoted at a concentration of $1 \times 10^4$ cells/well, treated with 5 μg/mL of the anti-MVR antibodies or mouse IgG, and cultured.

Figure 10:
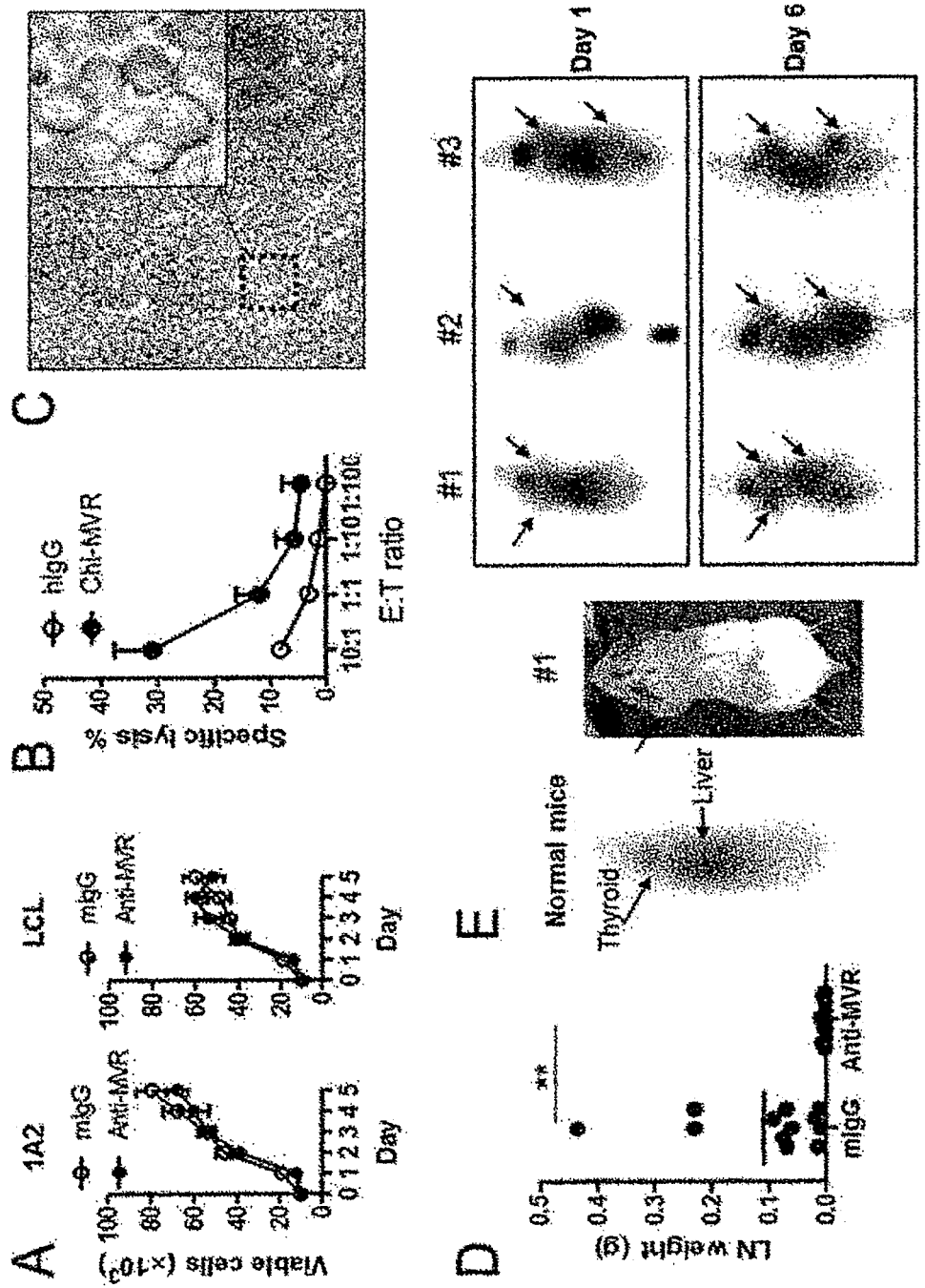
FIGS. 10 A to E shows the results illustrating in vitro and in vivo effects of the ChiMVR antibody on cancer cell growth, and the arrows in FIG. 10E showing positions of lymph nodes in the assessments in experimental example 6.

The number of live cells were measured using 4% Trypan blue solution daily for five days, and as a result, it was confirmed that the addition of the anti-MVR antibodies showed no affect on the proliferation of 1A2 or LCL (FIG. 10A). Accordingly, it was determined that the anti-MVR antibody has no direct impact on the proliferation of B cell lymphoma cells.

Additionally, when LCL cells were injected subcutaneously on the back of an immune-deficient mouse, $RAG2^{-/-}c^{-/-}$, the LCL cells temporarily proliferated at the injected area, but, in about four weeks thereafter, cancer tissues disappeared from the injected region, and metastasized into an adjacent lymph node, i.e., the inguinal lymph node or the axillary lymph node, and proliferated. Accordingly, eight weeks after cancer cell injection, the inguinal lymph node or the axillary lymph node was separated, and frozen after adding it into an OCT compound to prepare sections. Then, the thus prepared frozen tissue sections were stained with anti-MVR antibodies and anti-mouse IgG-HRP antibodies, and developed using DAB substrate.

As a result, it was confirmed that, in most cells constituting lymph nodes, the lymph nodes were enlarged due to the proliferation of LCL cells which were metastasized into positive state. The phenomenon was determined to be due to the proliferation of part of cancer cells after their metastasis into lymph nodes while the LCL cancer cells injected subcutaneously on the back temporarily proliferated (FIG. 10C).

Additionally, the LCL cancer cells were injected subcutaneously on the back of an immune-deficient mouse, $RAG2^{-/-}\gamma c^{-/-}$, and from the $7^{th}$ day after the cancer cell injection, the anti-MVR monoclonal antibodies were intraperitoneally injected daily at 5 day intervals. From the eighth week after the cancer cell injection, the inguinal lymph node or axillary lymph node was separated, and weighed to measure the growth of cancer cells.

As a result, when the immune-deficient $RAG2^{-/-}c^{-/-}$ mouse was injected subcutaneously on the back with LCL cancer cells, and then intraperitoneally administered with the anti-MVR antibodies from the $7^{th}$ day at 5 day intervals, the phenomenon of lymph node enlargement was inhibited (FIG. 10E). The phenomenon suggests that when the anti-MVR antibodies conjugate to the LCL cells, the metastasis of the LCL cells into lymph nodes may be inhibited.

Additionally, the LCL cells were injected subcutaneously on the back of the immune-deficient $RAG2^{-/-}\gamma c^{-/-}$ mouse, and seven weeks thereafter, was intravenously injected with $^{131}I$-labeled anti-MVR antibodies. On the $1^{st}$ day and the $6^{th}$ day after the antibody injection, each mouse was photographed using ADAC argus gamma camera equipped with a pinhole collimator, and observed whether the antibodies selectively conjugated to the cancer cells.

The result revealed that the anti-MVR antibodies were non-specifically accumulated in the thyroid gland and liver but were observed to be selectively conjugated to cancer cells and maintained the conjugation for at least six days (FIG. 10D).

EXPERIMENTAL EXAMPLE 7

Confirmation of Anticancer Effect of MVR-CAR CD8 T Cells Against B Cell Lymphoma Antigen-specific CD8$^{|}$T cells have been evaluated as most effective immune cells in immunological treatment of cancer. However, the separation of the antigen-specific CD8$^{+}$T cells for use in the immunological treatment of cancer requires a complicated process and a long term period. As such, as a method of a large scale production of the antigen-specific CD8$^{+}$T cells within a short period of time, chimeric antigen receptor (CAR)-modified T cells were proposed (Porter DL et al., N Engl J Med. 2011; 365:725-33.). CAR is a protein which conjugates the scFv of an antibody to a signaling domain that induces the activation of a T cell, and preferably, to the signaling domain of a co-stimulating molecule and CD3ξ. The principle is that when the antibody moiety constituting the CAR recognizes a particular antigen, it induces a strong signaling for T cell proliferation thereby selectively proliferating CD8 T cells (FIG. 11)

Figure 11:
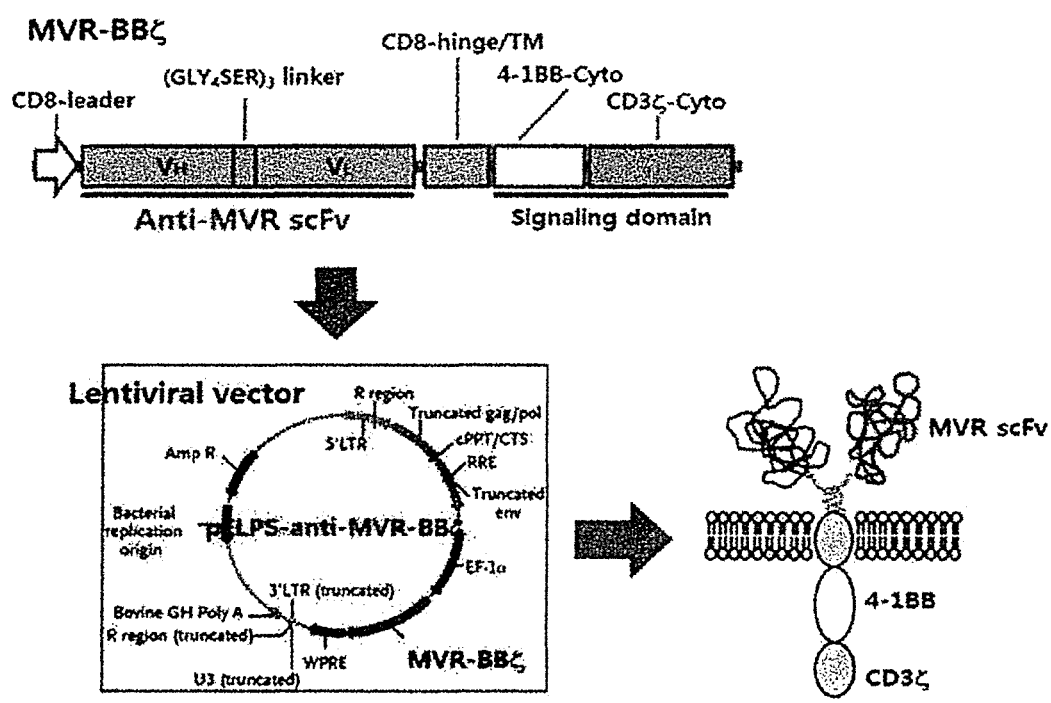
FIG. 11 shows a schematic diagram of a vector for MVR-BBξ, the CAR of the present invention.

Accordingly, in the present invention, the $V_H$ and $L_H$ parts of the anti-MVR antibody were connected via a $(GLY4SER)_3$ linker to construct an anti-MVR scFv, and then using CD8-hinge as a transmembrane domain, and sequentially connected the 4-1BB intracellular domain (cytoplasmic domain) and the intracellular domain of the CD3ξ chain to prepare an MVR-CAR (SEQ ID NO: 53) (FIG. 11). Specifically, it consists of CD8αleader sequence (SEQ ID NO: 55), anti-MVR VL & GlySer linker & anti-MVR VH (SEQ ID NO: 56), CD8α (spanning from hinge region to transmembrane region) (SEQ ID NO: 57), 4-1BB signaling domain (SEQ ID NO: 58), and TCRξ signaling domain (SEQ ID NO: 59). MVR-CAR was constituted such that MVR-CAR gene can be introduced into a CD8 T cell by inserting into pELPS, which is a lentivirus vector, using lentivirus, and the vector was named as pELPS-IRC5-BBξ.

The above constructed pELPS-IRC5-BBξ DNA was introduced into 293 cells, and cultured for five days to produce MVR-CAR lentivirus. The lentivirus in the culture supernatant was concentrated via Lenti-X$^{502}$ Concentrator (Clontech) to introduce the MVR-CAR gene into a T cell.

Additionally, peripheral blood mononuclear cells (PBMC) were separated from the blood of a normal volunteer, and only CD8$^+$T cells were separated using CD8-microbeads (Miltenyi Biotec). The separated CD8$^+$T cells were added with Dynal-beads coated with the anti-CD3 mAb and anti-CD28, and cultured for two days. On the 2$^{nd}$ day of the culture, the concentrated MVR-CAR/lentivirus was added at varied concentrations, and cultured for five days, and the MVR-CAR expression level of the CD8$^+$T cells was measured using protein L, which has been known to recognize the LH region of the light chain.

Figure 12:
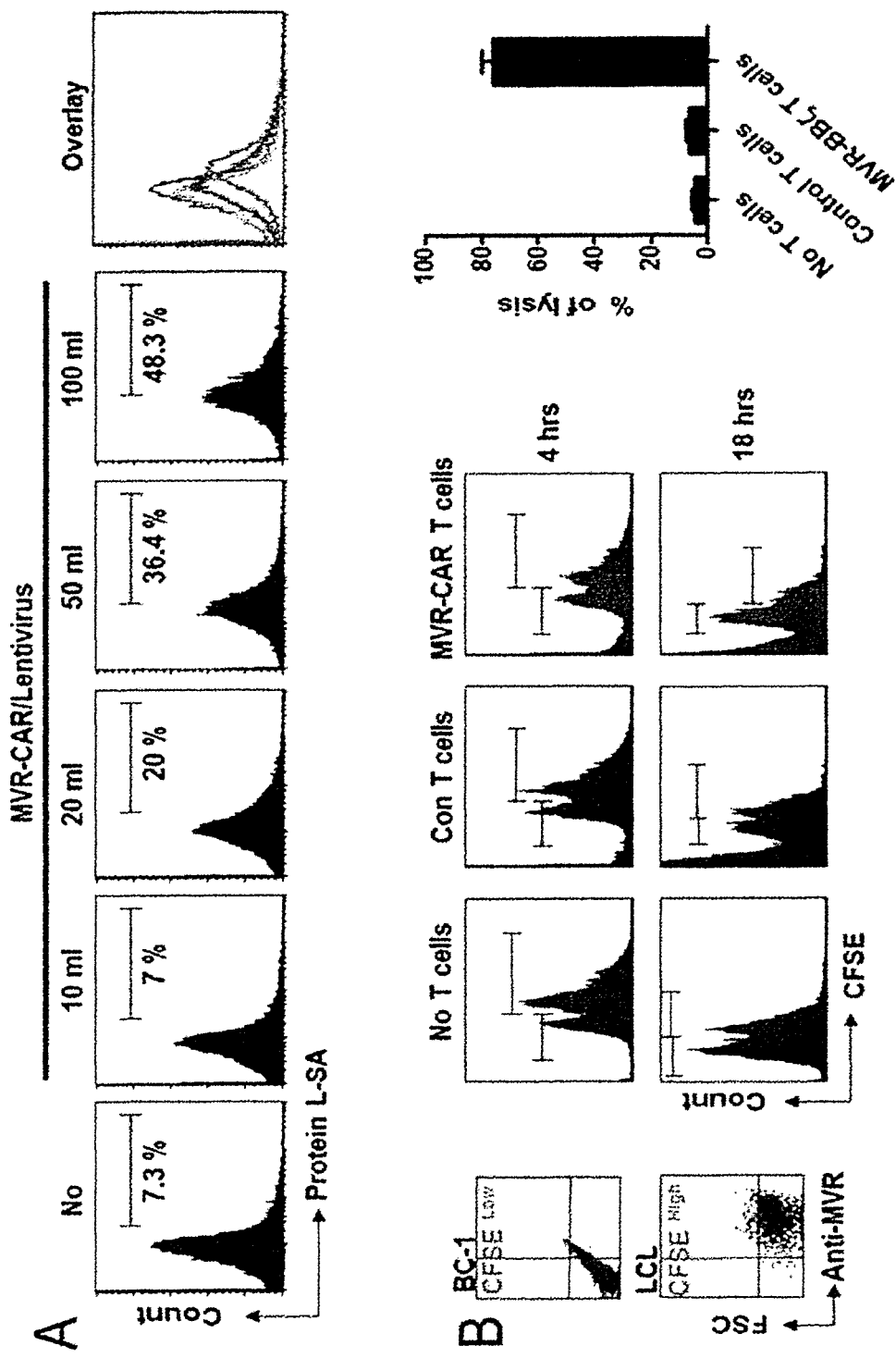
FIG. 12 shows the images illustrating the anti-cancer activity of T cells modified by MVR-BBξ, the CAR of the present invention.

As a result of flow cytometry analysis, it was confirmed that as the amount of the added MVR-CAR/lentivirus increased the reactivity to protein L increased (FIG. 12A). Accordingly, the constructed MVR-CAR was determined to be successfully expressed in the CD8$^+$T cells.

In order to evaluate the capability of CD8 T cells, which express the MVR-CAR, for selectively removing of cancer cells, BC-1 cells and LCL, which are MVR-positive and MVR-negative cancer cells, were prepared, and stained with CFSE at different concentrations, to distinguish the two different kinds of cells. The cells were mixed at 1:1 ratio, and then at 1:1 ratio with CD8 T cells, which were infected with MVR-CAR/lentivirus, cultured for 4 hours or 18 hours, and subjected to flow cytometry analysis. The lysis % was calculated by measuring the selective reduced ratio of the CFSE$^{high}$ MVR-positive LCL cells.

As a result, it was confirmed that the T cells in the control group did not reduce the ratio of the MVR-positive LCL, whereas the MVR-CAR CD8 T cells of the present invention selectively reduced the ratio of the MVR-positive LCL (FIG. 12B).

The above results suggest that the CD8 T cells, which overexpressed the MVR-CAR, can selectively recognize only the MVRpositive LCL and remove them, and thus they can be effectively used in the treatment of B cell lymphoma.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A method for treating B cell lymphoma in a human subject in need thereof, the method comprising administering a pharmaceutically effective amount of a composition, the composition comprising a monoclonal antibody specific to B cell lymphoma to the human subject, the monoclonal antibody comprising:
   a heavy chain variable region comprising a heavy chain CDR1 comprising the amino acid sequence of SEQ ID NO: 2; a heavy chain CDR2 comprising the amino acid sequence of SEQ ID NO: 3; and a heavy chain CDR3 comprising the amino acid sequence of SEQ ID NO: 4; and
   a light chain variable region comprising a light chain CDR1 comprising the amino acid sequence of SEQ ID NO: 6; a light chain CDR2 comprising the amino acid sequence of SEQ ID NO: 7; and a light chain CDR3 comprising the amino acid sequence of SEQ ID NO: 8.

2. The method of claim 1, wherein the monoclonal antibody comprises a heavy chain variable region comprising the amino acid sequence of SEQ ID NO: 1 and a light chain variable region comprising the amino acid sequence of SEQ ID NO: 5.

3. The method of claim 1, wherein the monoclonal antibody is in the form of a full-length antibody or an antibody fragment.

4. The method of claim 3, wherein the antibody fragment is selected from the group consisting of single chain variable fragment (scFv), dsFv, Fab, Fab', and F(ab')2.

5. The method of claim 1, wherein the monoclonal antibody comprises a heavy chain constant region selected from the group consisting of human IgG1, IgG2, IgG3, IgG4, IgA, IgE, IgM, and IgD.

6. The method of claim 1, wherein a pharmaceutical composition comprising the monoclonal antibody of claim 1 and a pharmaceutically acceptable carrier is administered to the human subject.

7. The method of claim 1, wherein the monoclonal antibody is conjugated to a drug.

8. The method of claim 7, wherein the drug is selected from the group consisting of an inhibitor of microtubulin structure formation, meiosis inhibitor, meiosis inhibitor, topoisomerase inhibitor, DNA intercalators, toxin, and radionuclides.

9. The method of claim 1, wherein the human subject has B cell lymphoma or the human subject is diagnosed of having B cell lymphoma.

10. The method of claim 1, wherein the composition is administered in the form of a liquid formulation, powder formulation, an aerosol, a capsule formulation, an enteric-coated tablet or capsule, or suppository formulation.

11. The method of claim 1, wherein the composition is administered by intraperitoneal administration, intravenous administration, intramuscular administration, subcutaneous administration, intracutaneous administration, oral administration, topical administration, intranasal administration, intrapulmonary administration, and intrarectal administration.

* * * * *